(12) United States Patent
Locke et al.

(10) Patent No.: US 10,143,485 B2
(45) Date of Patent: Dec. 4, 2018

(54) DEBRIDING DRESSING FOR USE WITH NEGATIVE PRESSURE AND FLUID INSTILLATION

(71) Applicant: KCI Licensing, Inc., San Antonio, TX (US)

(72) Inventors: Christopher Brian Locke, Bournemouth (GB); Peter Arnold, Northumberland (GB); Timothy Mark Robinson, Basingstoke (GB)

(73) Assignee: KCI Licensing, Inc., San Antonio, TX (US)

(*) Notice: Subject to any disclaimer, the term of this patent is extended or adjusted under 35 U.S.C. 154(b) by 521 days.

(21) Appl. No.: 14/708,078

(22) Filed: May 8, 2015

(65) Prior Publication Data

US 2015/0320603 A1   Nov. 12, 2015

Related U.S. Application Data

(60) Provisional application No. 61/991,134, filed on May 9, 2014.

(51) Int. Cl.
*A61B 17/32* (2006.01)
*A61F 13/00* (2006.01)
(Continued)

(52) U.S. Cl.
CPC .......... *A61B 17/32* (2013.01); *A61B 17/3205* (2013.01); *A61F 13/00017* (2013.01);
(Continued)

(58) Field of Classification Search
CPC ........... A61F 13/00017; A61B 17/3205; A61B 17/32
See application file for complete search history.

(56) References Cited

U.S. PATENT DOCUMENTS 1,355,846 A  10/1920  Rannells
2,547,758 A  4/1951  Kelling
(Continued)

FOREIGN PATENT DOCUMENTS

AU  550575 B2  3/1986
AU  745271 B2  3/2002
(Continued)

OTHER PUBLICATIONS

"Introduction to Polyurethanes: Thermoplastic Polyurethane", American Chemistry Council, https://polyurethane.americanchemistry.com/polyurethanes/Introduction-to-Polyurethanes/Applications/Thermoplastic-Polyurethane/.*
(Continued)

*Primary Examiner* — Tatyana Zalukaeva
*Assistant Examiner* — Gabriella Burnette

(57) ABSTRACT

Systems, methods, and apparatuses for debriding a tissue site are described. The system includes a manifold and a cover adapted to form a sealed space over the tissue site for providing negative pressure. The system also includes a debridement tool positioned between the manifold and the tissue site. The debridement tool having a tissue-facing surface and a plurality of holes separated from each other by walls. The walls have transverse surfaces extending between the tissue-facing surface and an opposite surface that form cutting edges. The holes have a perforation shape factor that allows the holes to collapse from a relaxed position to a contracted position in response to the application and removal of negative pressure from the sealed space. The cutting edges debride the tissue site in response to movement between the relaxed position and the contracted position.

22 Claims, 13 Drawing Sheets

(51) Int. Cl.
*A61M 1/00* (2006.01)
*A61L 31/14* (2006.01)
*A61B 17/3205* (2006.01)
*A61F 13/02* (2006.01)
*A61B 17/00* (2006.01)
*A61L 31/06* (2006.01)

(52) U.S. Cl.
CPC .... *A61F 13/00068* (2013.01); *A61F 13/0216* (2013.01); *A61L 31/06* (2013.01); *A61L 31/146* (2013.01); *A61M 1/0088* (2013.01); *A61B 2017/00761* (2013.01); *A61B 2017/320004* (2013.01); *A61B 2017/32006* (2013.01); *A61B 2017/320008* (2013.01); *A61F 2013/0028* (2013.01); *A61F 2013/00174* (2013.01); *A61L 2400/00* (2013.01); *A61M 1/0037* (2013.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2001/0037118 A1 | 11/2001 | Shadduck |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2009/0093779 A1 | 4/2009 | Riesinger |
| 2010/0063484 A1 | 3/2010 | Heagle |
| 2010/0160871 A1* | 6/2010 | Seegert .......... A61B 17/30 604/290 |
| 2010/0185163 A1 | 7/2010 | Heagle |
| 2011/0213319 A1 | 9/2011 | Blatt et al. |
| 2014/0066868 A1 | 3/2014 | Freedman et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |

(56) References Cited

FOREIGN PATENT DOCUMENTS

| WO | 87/04626 A1 | 8/1987 |
|---|---|---|
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 2008005532 A2 | 1/2008 |
| WO | 2009021523 A1 | 2/2009 |
| WO | 2014014922 A1 | 1/2014 |

OTHER PUBLICATIONS

Extended European Search Report for corresponding Application No. 171862527, dated Nov. 14, 2017.
Louis C. Argenta, MD and Michael J. Morykwas, PHD; Vacuum-Assisted Closure: A New Method for Wound Control and Treatment: Clinical Experience; Annals of Plastic Surgery.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. YU.N., et al; "Active Wound Drainage", Vestnki Khirurgi, vol. 138, Issue 4, 1987, and 7 page English translation thereof.
Davydov, YU.A., et al; "Bacteriological and Cytological Assessment of Vacuum Therapy for Purulent Wounds"; Vestnik Khirugi, Oct. 1988, pp. 48-52, and 8 page English translation thereof.
Davydov, YU.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164.
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Clinicians Guidelines; A Reference Source for Clinicians; Jul. 2007.
Partial International Search Report from PCT/US2015/030030 dated Jul. 22, 2015.

(56) References Cited

OTHER PUBLICATIONS

International Search Report and Written Opinion for PCT/US2015/030023 dated Aug. 24, 2015.

* cited by examiner

DEBRIDING DRESSING FOR USE WITH NEGATIVE PRESSURE AND FLUID INSTILLATION

The present invention claims the benefit, under 35 USC § 119(e), of the filing of U.S. Provisional Patent Application Ser. No. 61/991,134, entitled "Debriding Dressing for use with Negative Pressure and Fluid Instillation," by Locke et al., filed May 9, 2014, which is incorporated herein by reference for all purposes.

TECHNICAL FIELD

The invention set forth in the appended claims relates generally to tissue treatment systems and more particularly, but without limitation, to a dressing for debriding a tissue site.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," and "vacuum-assisted closure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, the cost and complexity of negative-pressure therapy can be a limiting factor in its application, and the development and operation of negative-pressure systems, components, and processes continue to present significant challenges to manufacturers, healthcare providers, and patients.

BRIEF SUMMARY

New and useful systems, apparatuses, and methods for debriding tissue in a negative-pressure therapy environment are set forth in the appended claims. Illustrative embodiments are also provided to enable a person skilled in the art to make and use the claimed subject matter. For example, a system is described herein that includes a manifold adapted to deliver negative pressure to the tissue site. The system may also include a cover adapted to form a sealed space over the manifold and the tissue site for receiving a negative pressure from a negative-pressure source. The system can further include a debridement tool positioned between the manifold and the tissue site. The debridement tool may have a tissue-facing surface and an opposite surface and a plurality of holes extending therebetween. The holes can be separated from each other by walls, which may have transverse surfaces extending between the tissue-facing surface and the opposite surface. The transverse surfaces may form cutting edges with the tissue-facing surface. The holes may have a perforation shape factor that allows the holes to collapse from a relaxed position to a contracted position in response to the application and removal of negative pressure to the sealed space. The cutting edges can debride the tissue site in response to movement of the debridement tool between the relaxed position and the contracted position.

Alternatively, another example embodiment includes an apparatus debriding a tissue site. The apparatus may include a debridement tool having a tissue-facing surface and an opposite surface including a plurality of holes extending therebetween. The holes may be separated from each other by walls, and the walls may have transverse surfaces extending between the tissue-facing surface and the opposite surface that form cutting edges with the tissue-facing surface. The holes may have a perforation shape factor that allows the holes to collapse from a relaxed position to a contracted position in response to the application and removal of negative pressure. The cutting edges can debride the tissue site in response to movement of the debridement tool between the relaxed position and the contracted position.

A method is also described herein, wherein some example embodiments include a method for debriding a tissue site. In some embodiments, a debridement tool may be positioned so that a tissue-facing surface of the debridement tool is adjacent to and covering the tissue site. The debridement tool may have a plurality of holes extending between the tissue-facing surface and an opposite surface that are separated from each other by walls. The walls may have transverse surfaces extending between the tissue-facing surface and the opposite surface that form cutting edges with the tissue-facing surface. The holes may have a perforation shape factor and a strut angle that allows the holes to collapse from a relaxed position to a contracted position generally perpendicular to a line of symmetry of the debridement tool. A sealing member may be positioned over the debridement tool and sealed to tissue surrounding the tissue site to form a sealed space having the debridement tool therein. A negative-pressure source may be fluidly coupled to the sealed space and negative pressure may be supplied to the sealed space to contract the debridement tool. Negative pressure may be vented from the sealed space to expand the debridement tool.

A system for treating a tissues site is also described herein, The system can include a manifold adapted to deliver negative pressure to the tissue site and having a first firmness factor. The system can also include a cover adapted to form a sealed space over the manifold and the tissue site for receiving a negative pressure from a negative-pressure source. In some embodiments, the system can include a tissue interface adapted to be positioned between the manifold and the tissue site. The tissue interface can have a second firmness factor that is greater than the first firmness factor and a plurality of holes separated from each other by walls.

Objectives, advantages, and a preferred mode of making and using the claimed subject matter may be understood best by reference to the accompanying drawings in conjunction with the following detailed description of illustrative embodiments.

BRIEF DESCRIPTION OF THE DRAWINGS

FIG. 1A is a detail view of a portion of the negative-pressure therapy system of FIG. 1;

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
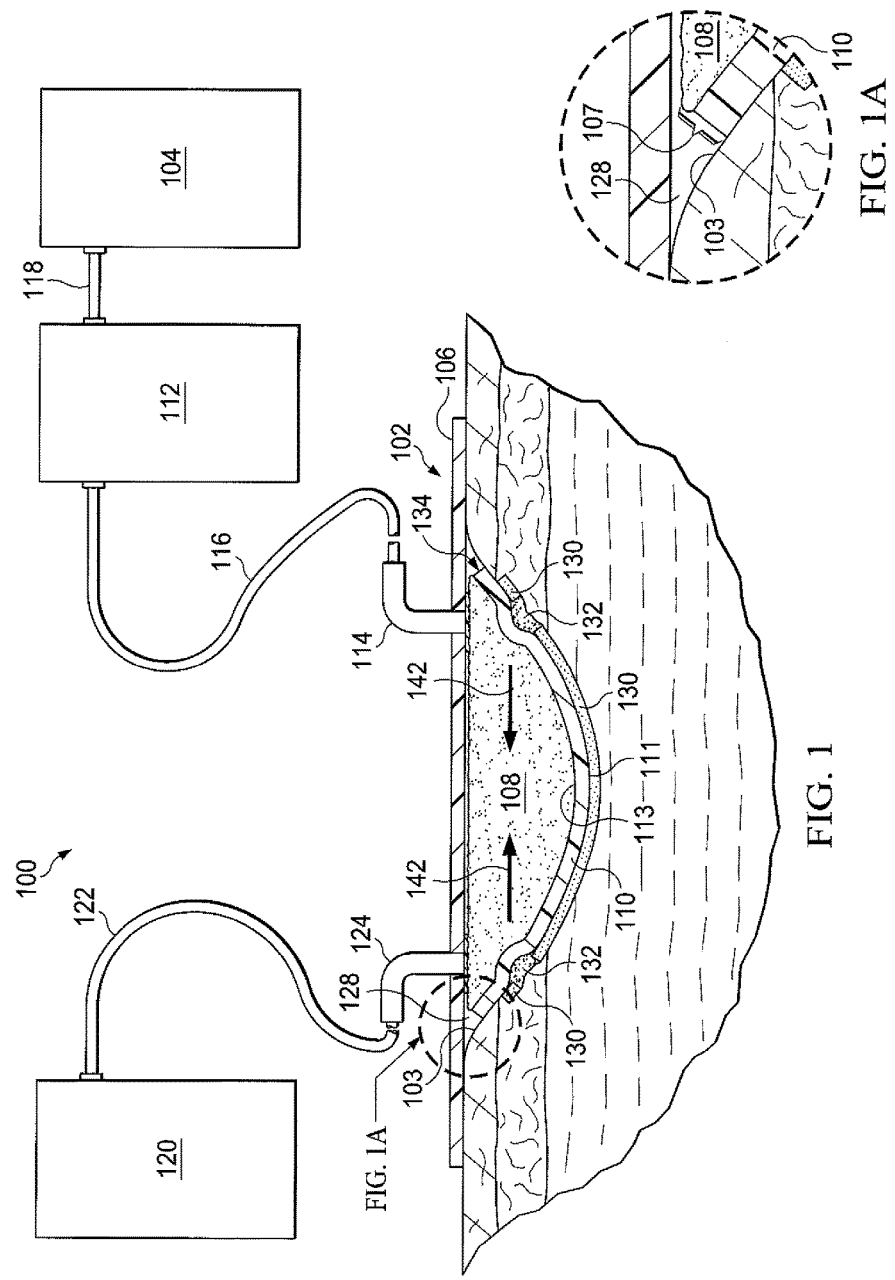
FIG. 1 is a sectional section view with a portion shown in elevation, illustrating details that may be associated with some embodiments of a negative-pressure therapy system.

FIG. 1 is a sectional view with a portion shown in elevation, of an example embodiment of a therapy system 100 that can provide negative pressure therapy, instillation of topical treatment solutions, and debridement in accordance with this specification. The therapy system 100 may include a dressing and a negative-pressure source. For example, a dressing 102 may be fluidly coupled to a negative-pressure source 104, as illustrated in FIG. 1. FIG. 1A is a detail view of a portion of the therapy system 100 of FIG. 1. As shown in FIG. 1 and FIG. 1A, the dressing 102, for example, includes a cover 106, and a tissue interface 107 for positioning adjacent or proximate a tissue site such as, for example, a tissue site 103. In some embodiments, the tissue interface 107 may be a manifold, for example, a manifold 108. In some embodiments, the tissue interface 107 may be a tissue removal tool, such as a debridement tool 110 having a tissue-facing surface 111 adapted to face the tissue site 103 and an opposite surface 113 adapted to face, for example, the manifold 108. In still other embodiments, the tissue interface 107 may be both the debridement tool 110 and the manifold 108. The therapy system 100 may also include an exudate container, such as a container 112, coupled to the dressing 102 and to the negative-pressure source 104, In some embodiments, the container 112 may be fluidly coupled to the dressing 102 by a connector 114 and a tube 116, and the container 112 may be fluidly coupled to the negative-pressure source 104 by a tube 118.

In some embodiments, the therapy system 100 may also include an installation solution source. For example, a fluid source 120 may be fluidly coupled to the dressing 102 by a tube 122 and a connector 124, as illustrated in the example embodiment of FIG. 1.

In general, components of the therapy system 100 may be coupled directly or indirectly. For example, the negative-pressure source 104 may be directly coupled to the container 112 and indirectly coupled to the dressing 102 through the container 112. Components may be fluidly coupled to each other to provide a path for transferring fluids (i.e., liquid and/or gas) between the components.

In some embodiments, for example, components may be fluidly coupled through a tube, such as the tube 116, the tube 118, and the tube 122. A "tube," as used herein, broadly refers to a tube, pipe, hose, conduit, or other structure with one or more lumina adapted to convey a fluid between two ends. Typically, a tube is an elongated, cylindrical structure with some flexibility, but the geometry and rigidity may vary. In some embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts.

A "connector," such as the connector 114 and the connector 124, may be used to fluidly couple a tube to a sealed therapeutic environment. The negative pressure developed by a negative-pressure source may be delivered through a tube to a connector. In one illustrative embodiment, a connector may be a T.R.A.C.® Pad or Sensa T.R.A.C.® Pad available from KCI of San Antonio, Tex. In one exemplary embodiment, the connector 114 may allow the negative pressure generated by the negative-pressure source 104 to be delivered to the sealed therapeutic environment 128. In other exemplary embodiments, a connector may also be a tube inserted through a drape. In one exemplary embodiment, the connector 124, may allow fluid provided by the fluid source 120 to be delivered to the sealed therapeutic environment 128.

In operation, the tissue interface 107 may be placed within, over, on, or otherwise proximate to the tissue site 103. The cover 106 may be placed over the tissue interface 107 and sealed to tissue near the tissue site. For example, the cover 106 may be sealed to undamaged epidermis peripheral to a tissue site, also known as peritissue. Thus, the dressing 102 can provide a sealed therapeutic environment 128 proximate to a tissue site, substantially isolated from the external environment, and the negative-pressure source 104 can reduce the pressure in the sealed therapeutic environment 128. Negative pressure applied across the tissue site 103 through the tissue interface 107 in the sealed therapeutic environment 128 can induce macrostrain and microstrain in the tissue site 103, as well as remove exudates and other fluids from the tissue site 103, which can be collected in container 112 and disposed of properly.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art.

In general, fluids flow toward lower pressure along a fluid path. Thus, the term "downstream" typically refers to a position in a fluid path that is closer to a source of negative pressure or alternatively further away from a source of positive pressure. Conversely, the term "upstream" refers to a position in a fluid path further away from a source of negative pressure or closer to a source of positive pressure. Similarly, it may be convenient to describe certain features in terms of fluid "inlet" or "outlet" in such a frame of reference, and the process of reducing pressure may be described illustratively herein as "delivering," "distributing," or "generating" reduced pressure, for example. This orientation is generally presumed for purposes of describing various features and components of systems herein.

The term "tissue site," such as the tissue site 103, in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of tissue that are not necessarily wounded or defective, but are instead areas in which it may be desirable to add or promote the growth of additional tissue. For example, negative pressure may be used in certain tissue areas to grow additional tissue that may be harvested and transplanted to another tissue location.

"Negative pressure" generally refers to a pressure less than a local ambient pressure, such as the ambient pressure in a local environment external to a sealed therapeutic environment provided by the dressing 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure.

A negative-pressure source, such as the negative-pressure source 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure source may be housed within or used in conjunction with other components, such as sensors, processing units, alarm indicators, memory, databases, software, display devices, or user interfaces that further facilitate negative-pressure therapy. While the amount and nature of negative pressure applied to a tissue site may vary according to therapeutic requirements, the pressure is generally a low vacuum, also commonly referred to as a rough vacuum, between −5 mmHg (−667 Pa) and −500 mmHg (−66.7 kPa). Common therapeutic ranges are between −75 mmHg (−9.9 kPa) and −300 mmHg (−39.9 kPa).

The tissue interface 107 can be generally adapted to contact a tissue site. The tissue interface 107 may be partially or fully in contact with the tissue site. If the tissue site is a wound, for example, the tissue interface 107 may partially or completely fill the wound, or may be placed over the wound. The tissue interface 107 may take many forms, and may have many sizes, shapes, or thicknesses depending on a variety of factors, such as the type of treatment being implemented or the nature and size of a tissue site. For example, the size and shape of the tissue interface 107 may be adapted to the contours of deep and irregular shaped tissue sites. In some embodiments, the tissue interface 107 may be provided in a spiral cut sheet. Moreover, any or all of the surfaces of the tissue interface 107 may have an uneven, coarse, or jagged profile that can induce microstrains and stresses at a tissue site.

In some embodiments, the tissue interface 107 may be a manifold, such as the manifold 108. A "manifold" in this context generally includes any substance or structure providing a plurality of pathways adapted to collect or distribute fluid across a tissue site under negative pressure. For example, a manifold may be adapted to receive negative pressure from a source and distribute the negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be channels interconnected to improve distribution or collection of fluids across a tissue site. For example, cellular foam, open-cell foam, reticulated foam, porous tissue collections, and other porous material such as gauze or felted mat generally include pores, edges, and/or walls adapted to form interconnected fluid pathways. Liquids, gels, and other foams may also include or be cured to include apertures and flow channels. In some illustrative embodiments, a manifold may be a porous foam material having interconnected cells or pores adapted to uniformly (or quasi-uniformly) distribute negative pressure to a tissue site. The foam material may be either hydrophobic or hydrophilic. The pore size of a foam material may vary according to needs of a prescribed therapy. For example, in some embodiments, the manifold 108 may be a foam having pore sizes in a range of about 400 microns to about 600 microns. The tensile strength of the manifold 108 may also vary according to needs of a prescribed therapy. For example, the tensile strength of a foam may be increased for instillation of topical treatment solutions. In one non-limiting example, the manifold 108 may be an open-cell, reticulated polyurethane foam such as GranuFoam® dressing available from Kinetic Concepts, Inc. of San Antonio, Texas; in other embodiments the manifold 108 may be an open-cell, reticulated polyurethane foam such as a VeraFlo® foam, also available from Kinetic Concepts, Inc., of San Antonio, Texas.

In an example in which the tissue interface 107 may be made from a hydrophilic material, the tissue interface 107 may also wick fluid away from a tissue site, while continuing to distribute negative pressure to the tissue site. The wicking properties of the tissue interface 107 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

In some embodiments, the tissue interface 107 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 107 may further serve as a scaffold for new cell-growth, or a scaffold material may be used in conjunction with the tissue interface 107 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 106 may provide a bacterial barrier and protection from physical trauma. The cover 106 may also be a sealing member constructed from a material that can reduce evaporative losses and provide a fluid seal between two components or two environments, such as between a therapeutic environment and a local external environment. The cover 106 may be, for example, an elastomeric film or membrane that can provide a seal adequate to maintain a negative pressure at a tissue site for a given negative-pressure source. In some example embodiments, the cover 106 may be a polymer drape, such as a polyurethane film, that is permeable to water vapor but impermeable to liquid. Such drapes typically have a thickness in the range of about 25 microns to about 50 microns. For permeable materials, the permeability generally should be low enough that a desired negative pressure may be maintained.

An attachment device may be used to attach the cover 106 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the cover 106 may be coated with an acrylic adhesive having a coating weight between about 25 grams per square meter (gsm) to about 65 gsm. Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The container 112 is representative of a container, canister, pouch, or other storage component that can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

The fluid source 120 may be representative of a container, canister, pouch, bag, or other storage component that can provide a solution for instillation therapy. Compositions of solutions may vary according to prescribed therapy, but examples of solutions that are suitable for some prescriptions include hypochlorite-based solutions, silver nitrate (0.5%), sulfur-based solutions, biguanides, cationic solutions, and isotonic solutions. In some embodiments, a fluid source, such as the fluid source 120, may be a reservoir of fluid at an atmospheric or greater pressure, or may be a manual or electrically-powered device, such as a pump, that can convey fluid to a sealed volume, such as the sealed therapeutic environment 128, for example. In some embodiments, a fluid source may include a peristaltic pump.

Some tissue sites may not heal according to the normal medical protocol and may develop areas of necrotic tissue. Necrotic tissue may be dead tissue resulting from infection, toxins, or trauma that caused the tissue to die faster than the tissue can be removed by the normal body processes that regulate the removal of dead tissue. Sometimes, necrotic tissue may be in the form of slough, which may include a viscous liquid mass of tissue. Generally, slough is produced by bacterial and fungal infections that stimulate an inflammatory response in the tissue. Slough may be a creamy yellow color and may also be referred to as pus. As shown in FIG. 1, slough, such as slough 130, may cover all or a portion of the tissue site 103. Necrotic tissue may also include eschar, such as eschar 132. Eschar 132 may be a portion of necrotic tissue that has become dehydrated and hardened. Eschar 132 may be the result of a burn injury, gangrene, ulcers, fungal infections, spider bites, or anthrax. Eschar may be difficult to move without the use of surgical cutting instruments. Necrotic tissue can also include thick exudate and fibrinous slough.

If a tissue site develops necrotic tissue, the tissue site may be treated with a process called debridement. Debridement may include the removal of dead, damaged, or infected material, such as thick exudate, fibrinous slough, the slough 130 or the eschar 132, from a tissue site. In some debridement processes, a mechanical process is used to remove necrotic tissue. Mechanical processes may include using scalpels or other cutting tools having a sharp edge to cut away the necrotic tissue from the tissue site. Typically, mechanical processes of debriding a tissue site may be painful and may require the application of local anesthetics.

Debridement may also be performed with an autolytic process. An autolytic process may involve using enzymes and moisture produced by a tissue site to soften and liquefy the necrotic tissue. Typically, a dressing may be placed over a tissue site having necrotic tissue so that fluid produced by the tissue site may remain in place, hydrating the necrotic tissue. Autolytic processes can be pain-free, but autolytic processes are a slow and can take many days. Because autolytic processes are slow, autolytic processes may also involve many dressing changes. Some autolytic processes may be paired with negative-pressure therapy so that, as necrotic tissue hydrates, negative pressure supplied to a tissue site may draw off the removed necrotic tissue. In some cases, a manifold positioned at a tissue site to distribute negative-pressure across the tissue site may become blocked or clogged with necrotic tissue broken down by an autolytic process. If a manifold becomes clogged, negative-pressure may not be able to draw off necrotic tissue, which can slow or stop the autolytic process.

Debridement may also be performed by adding enzymes or other agents to the tissue site. The enzymes digest tissue. Often, strict control of the placement of the enzymes and the length of time the enzymes are in contact with a tissue site must be maintained If enzymes are left on the tissue site for longer than needed, the enzymes may remove too much tissue, contaminate the tissue site, or be carried to other areas of a patient. Once carried to other areas of a patient, the enzymes may break down undamaged tissue and cause other complications.

These limitations and others may be addressed by the therapy system 100, which can provide negative-pressure therapy, instillation therapy, and debridement. For example, in some embodiments of the therapy system 100, a negative-pressure source may be fluidly coupled to a tissue site to provide negative pressure to the tissue site for negative-pressure therapy. In some embodiments, a fluid source may be fluidly coupled to a tissue site to provide therapeutic fluid to the tissue site for instillation therapy. In some embodiments, the therapy system 100 may include a debridement tool positioned adjacent to a tissue site. In some embodiments of the therapy system 100, a debridement tool may be used with negative-pressure therapy and instillation therapy to debride areas of a tissue site having necrotic tissue.

The therapy system 100 may be used on the tissue site 103 having the slough 130 and the eschar 132. In some embodiments, the debridement tool 110 may be positioned adjacent to the tissue site 103 so that the debridement tool 110 is in contact with the slough 130 and the eschar 132. In some embodiments, the manifold 108 may be positioned over the debridement tool 110. In other embodiments, if the tissue site 103 has a depth about a depth of the debridement tool 110, the manifold 108 may not be used.

In some embodiments, the debridement tool 110 may be a substantially flat or substantially planar body. The debridement tool 110 may have a thickness 134. In some embodiments, the thickness 134 may be about 15 mm. In other embodiments, the thickness 134 may be thinner or thicker than about 15 mm as needed for the tissue site 103. In some embodiments, individual portions of the debridement tool 110 may have a minimal tolerance from the thickness 134. In some embodiments, the thickness 134 may have a tolerance of about 2 mm. The debridement tool 110 may be flexible so that the debridement tool 110 can be contoured to a surface of the tissue site 103.

In some embodiments, the debridement tool 110 may be formed from thermoplastic elastomers (TPE), such as styrene ethylene butylene styrene (SEBS) copolymers, or thermoplastic polyurethane (TPU). The debridement tool 110 may be formed by combining sheets of TPE or TPU. In some embodiments, the sheets of TPE or TPU may be bonded, welded, adhered, or otherwise coupled to one another. For example, in some embodiments, the sheets of TPE or TPU may be welded using radiant heat, radio-frequency welding, or laser welding. Supracor, Inc., Hexacor, Ltd., Hexcel Corp., and Econocorp, Inc. may produce suitable TPE or TPU sheets for the formation of the debridement tool 110. In some embodiments, sheets of TPE or TPU having a thickness between about 0.2 mm and about 2.0 mm may be used to form a structure having the thickness 134. In some embodiments, the debridement tool 110 may be formed from a 3D textile, also referred to as a spacer fabric. Suitable 3D textiles may be produced by Heathcoat Fabrics, Ltd., Baltex, and Mueller Textil Group.

In some embodiments, the debridement tool 110 may be formed from a foam. For example, cellular foam, open-cell foam, reticulated foam, or porous tissue collections, may be used to form the debridement tool 110. In some embodiments, the debridement tool 110 may be formed of GranuFoam®, grey foam, or Zotefoam. Grey foam may be a polyester polyurethane foam having about 60 pores per inch (ppi). Zotefoam may be a closed-cell crosslinked polyolefin foam. In one non-limiting example, the debridement tool 110 may be an open-cell, reticulated polyurethane foam such as GranuFoam® dressing available from Kinetic Concepts, Inc. of San Antonio, Tex.; in other embodiments, the debridement tool 110 may be an open-cell, reticulated polyurethane foam such as a V.A.C. VeraFlo® foam, also available from Kinetic Concepts, Inc., of San Antonio, Tex.

In some embodiments, the debridement tool 110 may be formed from a foam that is mechanically or chemically compressed to increase the density of the foam at ambient pressure. A foam that is mechanically or chemically compressed may be referred to as a compressed foam. A compressed foam may be characterized by a firmness factor (FF) that is defined as a ratio of the density of a foam in a compressed state to the density of the same foam in an uncompressed state. For example, a firmness factor (FF) of 5 may refer to a compressed foam having a density that is five times greater than a density of the same foam in an uncompressed state. Mechanically or chemically compressing a foam may reduce a thickness of the foam at ambient pressure when compared to the same foam that has not been compressed. Reducing a thickness of a foam by mechanical or chemical compression may increase a density of the foam, which may increase the firmness factor (FF) of the foam. Increasing the firmness factor (FF) of a foam may increase a stiffness of the foam in a direction that is parallel to a thickness of the foam. For example, increasing a firmness factor (FF) of the debridement tool 110 may increase a stiffness of the debridement tool 110 in a direction that is parallel to the thickness 134 of the debridement tool 110. In some embodiments, a compressed foam may be a compressed GranuFoam®. GranuFoam® may have a density of about 0.03 grams per centimeter$^3$ (g/cm$^3$) in its uncompressed state. If the GranuFoam® is compressed to have a firmness factor (FF) of 5, the GranuFoam® may be compressed until the density of the GranuFoam® is about 0.15 g/cm$^3$. VeraFlo® foam may also be compressed to form a compressed foam having a firmness factor (FF) up to 5. In some embodiments, the debridement tool 110 may have a thickness of about 8 mm, and if the debridement tool 110 is positioned within the sealed therapeutic space 128 and subjected to negative pressure of about −125 mmHg, the thickness 134 of the debridement tool 110 may be greater than about 3 mm.

A compressed foam may also be referred to as a felted foam. As with a compressed foam, a felted foam undergoes a thermoforming process to permanently compress the foam to increase the density of the foam. A felted foam may also be compared to other felted foams or compressed foams by comparing the firmness factor of the felted foam to the firmness factor of other compressed or uncompressed foams. Generally a compressed or felted foam may have a firmness factor greater than 1.

The firmness factor (FF) may also be used to compare compressed foam materials with non-foam materials. For example, a Supracor® material may have a firmness factor (FF) that allows Supracor® to be compared to compressed foams. In some embodiments, the firmness factor (FF) for a non-foam material may represent that the non-foam material has a stiffness that is equivalent to a stiffness of a compressed foam having the same firmness factor. For example, if a debridement tool is formed from Supracor®, as illustrated in Table 1 below, the debridement tool may have a stiffness that is about the same as the stiffness of a compressed GranuFoam® material having a firmness factor (FF) of 3.

Generally, if a compressed foam is subjected to negative pressure, the compressed foam exhibits less deformation than a similar uncompressed foam. If the debridement tool 110 is formed of a compressed foam, the thickness 134 of the debridement tool 110 may deform less than if the debridement tool 110 is formed of a comparable uncompressed foam. The decrease in deformation may be caused by the increased stiffness as reflected by the firmness factor (FF). If subjected to the stress of negative pressure, the debridement tool 110 that is formed of compressed foam may flatten less than the debridement tool 110 that is formed from uncompressed foam. Consequently, when negative pressure is applied to the debridement tool 110, the stiffness of the debridement tool 110 in the direction parallel to the thickness 134 of the debridement tool 110 allows the debridement tool 110 to be more compliant or compressible in other directions, e.g., a direction perpendicular to the thickness 134. The foam material used to form a compressed foam may be either hydrophobic or hydrophilic The pore size of a foam material may vary according to needs of the debridement tool 110 and the amount of compression of the foam. For example, in some embodiments, an uncompressed foam may have pore sizes in a range of about 400 microns to about 600 microns. If the same foam is compressed, the pore sizes may be smaller than when the foam is in its uncompressed state.

Figure 2:
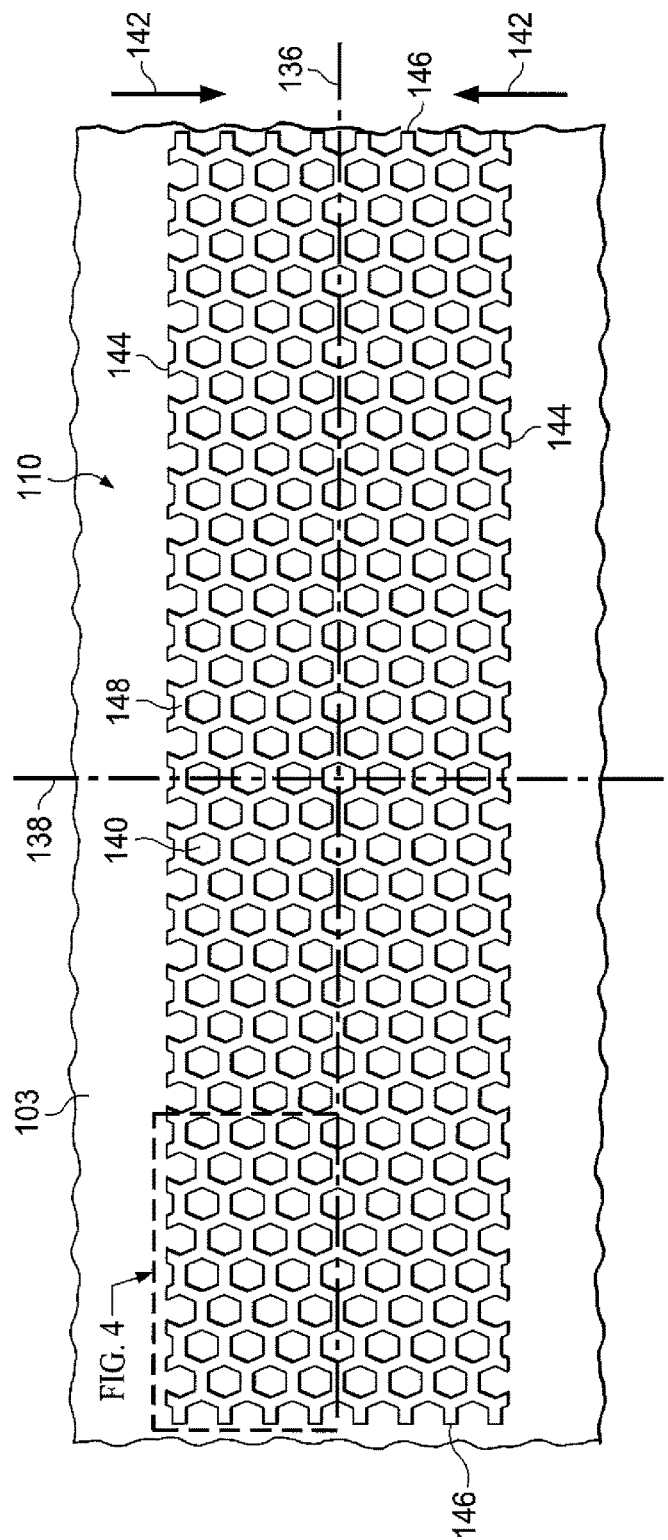
FIG. 2 is a plan view, illustrating details that may be associated with some embodiments of a debridement tool of the negative-pressure therapy system of FIG. 1 in a first position.

FIG. 2 is a plan view, illustrating additional details that may be associated with some embodiments of the debridement tool 110. The debridement tool 110 may include a plurality of holes 140 or perforations extending through the debridement tool 110 to form walls 148 extending through the debridement tool 110. In some embodiments, the walls 148 may be parallel to the thickness 134 of the debridement tool 110. In other embodiments, the walls 148 may be generally perpendicular to the tissue-facing surface 111 and the opposite surface 113 of the debridement tool 110. In some embodiments, the holes 140 may have a hexagonal shape as shown. In other embodiments, the holes 140 may have a circular, oval, triangular, square, irregular, or amorphous shape.

In some embodiments, the debridement tool 110 may have a first orientation 136 and a second orientation line 138 that is perpendicular to the first orientation line 136. The first orientation line 136 and the second orientation line 138 may be lines of symmetry of the debridement tool 110. A line of symmetry may be, for example, an imaginary line across the tissue-facing surface 111 or the opposite surface 113 of the debridement tool 110 defining a fold line such that if the debridement tool 110 is folded on the line of symmetry, the holes 140 and walls 148 would be coincidently aligned. Generally, the first orientation line 136 and the second orientation line 138 aid in the description of the debridement tool 110. In some embodiments, the first orientation line 136 and the second orientation line 138 may be used to refer to the desired directions of contraction of the debridement tool 110. For example, the desired direction of contraction may be parallel to the second orientation line 138 and perpendicular to the first orientation line 136. In other embodiments, the desired direction of contraction may be parallel to the first orientation line 136 and perpendicular to the second orientation line 138. In still other embodiments, the desired direction of contraction may be at a non-perpendicular angle to both the first orientation line 136 and the second orientation line 138. Generally, the debridement tool 110 may be placed at the tissue site 103 so that the second orientation line 138 extends across the slough 130 and the eschar 132 of FIG. 1.

Although the debridement tool 110 is shown as having a generally rectangular shape including longitudinal edges 144 and latitudinal edges 146, the debridement tool 110 may have other shapes. For example, the debridement tool 110 may have a diamond, square, or circular shape. In some embodiments, the shape of the debridement tool 110 may be selected to accommodate the type of tissue site being treated. For example, the debridement tool 110 may have an oval or circular shape to accommodate an oval or circular tissue site. In some embodiments, the first orientation line 136 may be parallel to the longitudinal edges 144.

Figure 3:
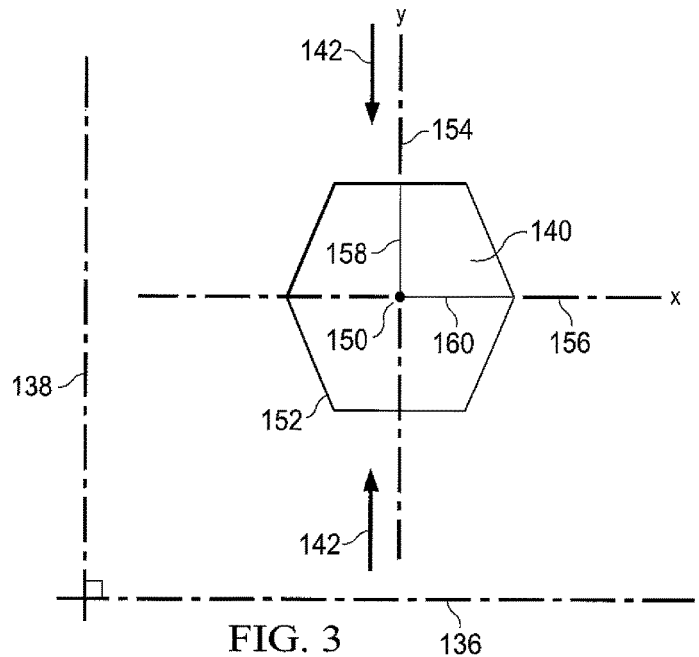
FIG. 3 is a schematic view, illustrating details that may be associated with some embodiments of a hole of the debridement tool of FIG. 2.

Referring more specifically to FIG. 3, a single hole 140 having a hexagonal shape is shown. The hole 140 may include a center 150 and a perimeter 152. The hole 140 may have a perforation shape factor (PSF). The perforation shape factor (PSF) may represent an orientation of the hole 140 relative to the first orientation line 136 and the second orientation line 138. Generally, the perforation shape factor (PSF) is a ratio of 1/2 a maximum length of the hole 140 that is parallel to the desired direction of contraction to 1/2 a maximum length of the hole 140 that is perpendicular to the desired direction of contraction. For descriptive purposes, the desired direction of contraction is parallel to the second orientation line 138. The desired direction of contraction may be indicated by a debriding force 142. For reference, the hole 140 may have an X-axis 156 extending through the center 150 between opposing vertices of the hexagon and parallel to the first orientation line 136, and a Y-axis 154 extending through the center 150 between opposing sides of the hexagon and parallel to the second orientation line 138. The perforation shape factor (PSF) of the hole 140 may be defined as a ratio of a line segment 158 on the Y-axis 154 extending from the center 150 to the perimeter 152 of the hole 140, to a line segment 160 on the X-axis 156 extending from the center 150 to the perimeter 152 of the hole 140. If a length of the line segment 158 is 2.69 mm and the length of the line segment 160 is 2.5 mm, the perforation shape factor (PSF) would be 2.69/2.5 or about 1.08. In other embodiments, the hole 140 may be oriented relative to the first orientation line 136 and the second orientation line 138 so that the perforation shape factor (PSF) may be about 1.07 or 1.1.

Figure 4:
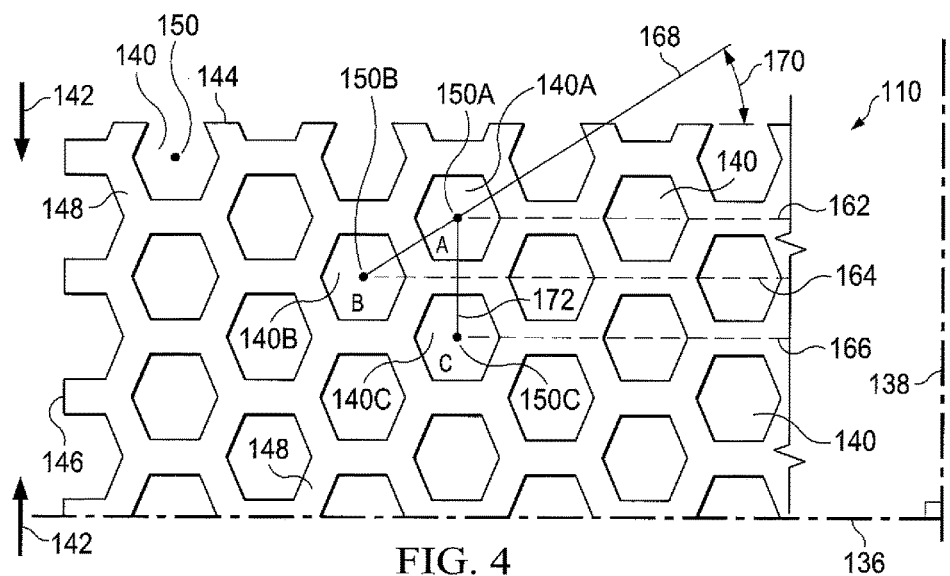
FIG. 4 is a plan view, illustrating details that may be associated with some embodiments of the holes of the debridement tool of FIG. 2.

Referring to FIG. 4, a portion of the debridement tool 110 of FIG. 1 is shown. The debridement tool 110 may include the plurality of holes 140 aligned in a pattern of parallel rows. The pattern of parallel rows may include a first row 162 of the holes 140, a second row 164 of the holes 140, and a third row 166 of the holes 140. The centers 150 of the holes 140 in adjacent rows, for example, the first row 162 and the second row 164, may be characterized by being offset from the second orientation line 138 along the first orientation line

136. In some embodiments, a line connecting the centers of adjacent rows may form a strut angle (SA) with the first orientation line 136. For example, a first hole 140A in the first row 162 may have a center 150A, and a second hole 140B in the second row 164 may have a center 150B. A strut line 168 may connect the center 150A with the center 150B. The strut line 168 may form an angle 170 with the first orientation line 136. The angle 170 may be the strut angle (SA) of the debridement tool 110. In some embodiments, the strut angle (SA) may be less than about 90°. In other embodiments, the strut angle (SA) may be between about 30° and about 70° relative to the first orientation line 136. In other embodiments, the strut angle (SA) may be about 66° from the first orientation line 136. Generally, as the strut angle (SA) decreases, a stiffness of the debridement tool 110 in a direction parallel to the first orientation line 136 may increase. Increasing the stiffness of the debridement tool 110 parallel to the first orientation line 136 may increase the compressibility of the debridement tool 110 perpendicular to the first orientation line 136. Consequently, if negative pressure is applied to the debridement tool 110, the debridement tool 110 may be more compliant or compressible in a direction perpendicular to the first orientation line 136. By increasing the compressibility of the debridement tool 110 in a direction perpendicular to the first orientation line 136, the debridement tool 110 may collapse to apply the debriding force 142 to the tissue site 103 described in more detail below.

In some embodiments, the centers 150 of the holes 140 in alternating rows, for example, the center 150A of the first hole 140A in the first row 162 and a center 150C of a hole 140C in the third row 166, may be spaced from each other parallel to the second orientation line 138 by a length 172. In some embodiments, the length 172 may be greater than an effective diameter of the hole 140. If the centers 150 of holes 140 in alternating rows are separated by the length 172, walls 148 parallel to the first orientation line 136 may be considered continuous. Generally, the walls 148 may be continuous if the walls 148 do not have any discontinuities or breaks between holes 140.

Regardless of the shape of the holes 140, the holes 140 in the debridement tool 110 may leave void spaces in the debridement tool 110 and on the tissue-facing surface 111 and the opposite surface 113 of the debridement tool 110 so that only the walls 148 of the debridement tool 110 remain with a surface available to contact the tissue site 103. It may be desirable to minimize the walls 148 so that the holes 140 may collapse, causing the debridement tool 110 to collapse and generate the debriding force 142 in a direction perpendicular to the first orientation line 136. However, it may also be desirable not to minimize the walls 148 so much that the debridement tool 110 becomes too fragile for sustaining the application of a negative pressure. The void space percentage (VS) of the holes 140 may be equal to the percentage of the volume or surface area of the void spaces of the tissue-facing surface 111 created by the holes 140 to the total volume or surface area of the tissue-facing surface 111 of the debridement tool 110. In some embodiments, the void space percentage (VS) may be between about 40% and about 60%. In other embodiments, the void space percentage (VS) may be about 55%.

In some embodiments, the holes 140 may be formed during molding of the debridement tool 110. In other embodiments, the holes 140 may be formed by cutting, melting, or vaporizing the debridement tool 110 after the debridement tool 110 is formed. For example, the holes 140 may be formed in the debridement tool 110 by laser cutting the compressed foam of the debridement tool 110. In some embodiments, an effective diameter of the holes 140 may be selected to permit flow of particulates through the holes 140. An effective diameter of a non-circular area is defined as a diameter of a circular area having the same surface area as the non-circular area. In some embodiments, each hole 140 may have an effective diameter of about 3.5 mm. In other embodiments, each hole 140 may have an effective diameter between about 5 mm and about 20 mm. The effective diameter of the holes 140 should be distinguished from the porosity of the material forming the walls 148 of the debridement tool 110. Generally, an effective diameter of the holes 140 is an order of magnitude larger than the effective diameter of the pores of a material forming the debridement tool 110. For example, the effective diameter of the holes 140 may be larger than about 1 mm, while the walls 148 may be formed from GranuFoam® material having a pore size less than about 600 microns. In some embodiments, the pores of the walls 148 may not create openings that extend all the way through the material.

Referring now to both FIGS. 2 and 4, the holes 140 may foam a pattern depending on the geometry of the holes 140 and the alignment of the holes 140 between adjacent and alternating rows in the debridement tool 110 with respect to the first orientation line 136. If the debridement tool 110 is subjected to negative pressure, the holes 140 of the debridement tool 110 may collapse. In some embodiments the void space percentage (VS), the perforation shape factor (PSF), and the strut angle (SA) may cause the debridement tool 110 to contract along the second orientation line 138 perpendicular to the first orientation line 136 as shown in more detail in FIG. 5. If the debridement tool 110 is positioned on the tissue site 103, the debridement tool 110 may generate the debriding force 142 along the second orientation line 138, contracting the debridement tool 110, as shown in more detail in FIG. 5. The debriding force 142 may be optimized by adjusting the factors described above as set forth in Table 1 below. In some embodiments, the holes 140 may be hexagonal, have a strut angle (SA) of approximately 66°, a void space percentage (VS) of about 55%, a firmness factor (FF) of about 5, a perforation shape factor (PSF) of about 1.07, and an effective diameter of about 5 mm. If the debridement tool 110 is subjected to a negative pressure of about −125 mmHg, the debriding force 142 asserted by the debridement tool 110 is about 13.3 N. If the effective diameter of the holes 140 of the debridement tool 110 is increased to 10 mm, the debriding force 142 is decreased to about 7.5 N.

Figure 5:
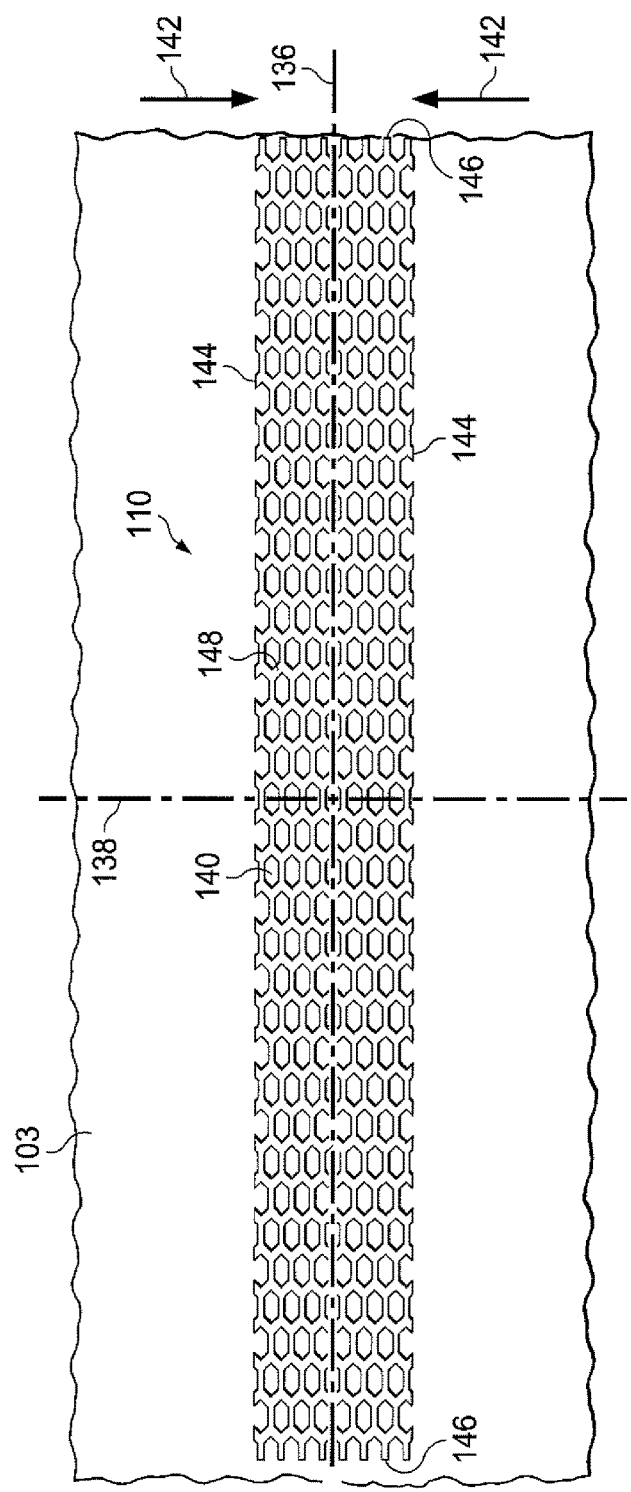
FIG. 5 is a plan view, illustrating details that may be associated with some embodiments of the debridement tool of FIG. 2 in a second position.

Referring to FIG. 5, the debridement tool 110 is in the second position, or contracted position, as indicated by the debriding force 142. In operation, negative pressure is supplied to the sealed therapeutic environment 128 with the negative-pressure source 104. In response to the supply of negative pressure, the debridement tool 110 contracts from the relaxed position illustrated in FIG. 2 to the contracted position illustrated in FIG. 5. Generally, the thickness 134 of the debridement tool 110 remains substantially the same. When the negative pressure is removed, for example, by venting the negative pressure, the debridement tool 110 expands back to the relaxed position. If the debridement tool 110 is cycled between the contracted and relaxed positions of FIGS. 5 and FIG. 2, respectively, the tissue-facing surface 111 of the debridement tool 110 debrides the tissue site 103 by cutting away dead or contaminated tissue from the wound, including the slough 130 and the eschar 132. The edges of the holes 140 formed by the tissue-facing surface 111 and transverse surfaces of the walls 148 form cutting edges that debride the tissue site 103, allowing the severed tissue to exit through the holes 140 and the manifold 108 into the container 112 when negative pressure is applied. In some embodiments, the cutting edges are defined by the perimeter 152 where each hole 140 intersects the tissue-facing surface 111.

In some embodiments, the therapy system 100 may provide cyclic therapy. Cyclic therapy may alternately apply negative pressure to and vent negative pressure from the sealed therapeutic environment 128. In some embodiments, negative pressure may be supplied to the sealed therapeutic environment 128 until the pressure in the sealed therapeutic environment 128 reaches a predetermined therapy pressure. If negative pressure is supplied to the sealed therapeutic environment 128, the debridement tool 110 contracts as shown in FIG. 5. In some embodiments, the sealed therapeutic environment 128 may remain at the therapy pressure for a predetermined therapy period such as, for example, about 10 minutes, In other embodiments, the therapy period may be longer or shorter as needed to supply appropriate negative-pressure therapy to the tissue site 103.

Following the therapy period, the sealed therapeutic environment 128 may be vented. For example, the negative-pressure source 104 may fluidly couple the sealed therapeutic environment 128 to the atmosphere (not shown), allowing the sealed therapeutic environment 128 to return to ambient pressure. In some embodiments, the negative-pressure source 104 may vent the sealed therapeutic environment 128 for about 1 minute. In other embodiments, the negative-pressure source 104 may vent the sealed therapeutic environment 128 for longer or shorter periods. In response to the return of the sealed therapeutic environment 128 to ambient pressure by venting the sealed therapeutic environment 128, the debridement tool 110 expands, returning to the relaxed position of FIG. 2. The contraction and expansion of the debridement tool 110 causes the cutting edges of the debridement tool 110 to debride the tissue site 103 as described above. Removed portions of the severed tissue, including the slough 130 and the eschar 132 may be drawn out through the holes 140 when negative pressure is applied to the sealed therapeutic environment 128 by the negative-pressure source 104.

In some embodiments, instillation therapy may be combined with negative-pressure therapy. For example, following the therapy period of negative-pressure therapy, the fluid source 120 may operate to provide fluid to the sealed therapeutic environment 128. In some embodiments, the fluid source 120 may provide fluid while the negative-pressure source 104 vents the sealed therapeutic environment 128. For example, the fluid source 120 may include a pump configured to move instillation fluid from the fluid source 120 to the sealed therapeutic environment 128. In other embodiments, the negative-pressure source 104 may not vent the sealed therapeutic environment 128. Instead, the negative pressure in the sealed therapeutic environment 128 is used to draw instillation fluid from the fluid source 120 into the sealed therapeutic environment 128.

In some embodiments, the fluid source 120 may provide a volume of fluid to the sealed therapeutic environment 128. In some embodiments, the volume of fluid may be the same as a volume of the sealed therapeutic environment 128. In other embodiments, the volume of fluid may be smaller or larger than the sealed therapeutic environment 128 as needed to appropriately apply instillation therapy. In some embodiments, the fluid provided by the fluid source 120 may remain in the sealed therapeutic environment 128 for a dwell time. In some embodiments, the dwell time is about 5 minutes. In other embodiments, the dwell time may be longer or shorter as needed to appropriately administer instillation therapy to the tissue site 103. The dwell time may be referred to as a dwell period of a therapy cycle.

At the conclusion of the dwell time, the negative-pressure source 104 may be operated to draw off the instillation fluid into the container 112, completing a cycle of therapy. As the instillation fluid is removed from the sealed therapeutic environment 128 with negative pressure, negative pressure may also be supplied to the sealed therapeutic environment 128, starting another cycle of therapy.

In each cycle of therapy provided by the negative-pressure source 104, the debridement tool 110 may be contracted and expanded. With each cycle of therapy, the tissue-facing surface 111 of the debridement tool 110 is rubbed across a facing surface of the tissue site 103 by the debriding force 142, The rubbing action of the debridement tool 110 by the debriding force 142 causes the cutting edges of the holes 140 to dislodge portions of the slough 130 and the eschar 132. With each subsequent cycle of therapy, additional portions of slough 130 and eschar 132 are removed from the tissue site 103 by the debriding force 142. The dislodged portions of the slough 130 and the eschar 132 in particles may be sufficiently small to be drawn-off from the tissue site 103 by negative-pressure therapy. If instillation therapy is also provided, the fluid from the fluid source 120 may also aid in the removal of debrided tissue. Instillation therapy may also clean the manifold 108, preventing blockage of the manifold 108 by removed slough 130 and eschar 132.

Figure 6:
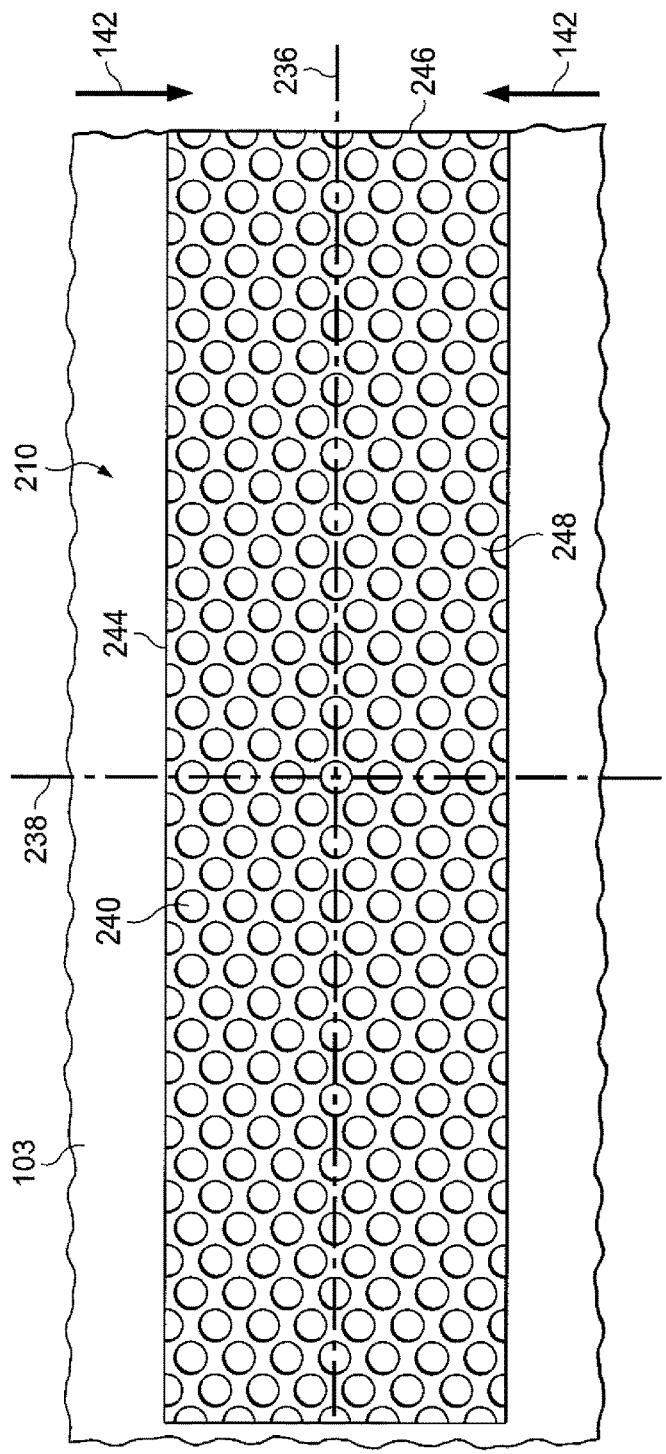
FIG. 6 is a plan view, illustrating details that may be associated with some embodiments of another debridement tool of the negative-pressure therapy system of FIG. 1.

FIG. 6 is a plan view, illustrating additional details that may be associated with some embodiments of a debridement tool 210. The debridement tool 210 may be similar to the debridement tool 110 and operate as described above with respect to FIGS. 1-5. Similar elements may have similar numbers indexed to 200. For example, the debridement tool 210 is shown as having a generally rectangular shape including longitudinal edges 244 and latitudinal edges 246. The debridement tool 210 may have a first orientation line 236 and a second orientation line 238 that is perpendicular to the first orientation line 236. In some embodiments, the first orientation line 236 and the second orientation line 238 may be used to refer to the desired directions of contraction for the debridement tool 210. For example, the desired direction of contraction may be parallel to the second orientation line 238 and perpendicular to the first orientation line 236, as shown by the debriding force 142. In other embodiments, the desired direction of contraction may be perpendicular to the second orientation line 238 and parallel to the first orientation line 236. In still other embodiments, the desired direction of contraction may be at a non-perpendicular to both the second orientation line 238 and the first orientation line 236. Generally, the debridement tool 210 may be placed at the tissue site 103 so that a tissue-facing surface 211 of the debridement tool 210 may cover portions of the tissue site 103 having slough 130 or eschar 132, The debridement tool 210 may include a plurality of holes 240 or perforations extending through the debridement tool 210 to from walls 248 that extend through the debridement tool 210. In some embodiments, the walls 248 are parallel to the thickness 234 of the debridement tool 210. The walls 248 may have transverse surfaces that intersect with the tissue-facing surface 211 to form cutting edges. In some embodiments, the holes 240 may have a circular shape as shown.

Figure 7:
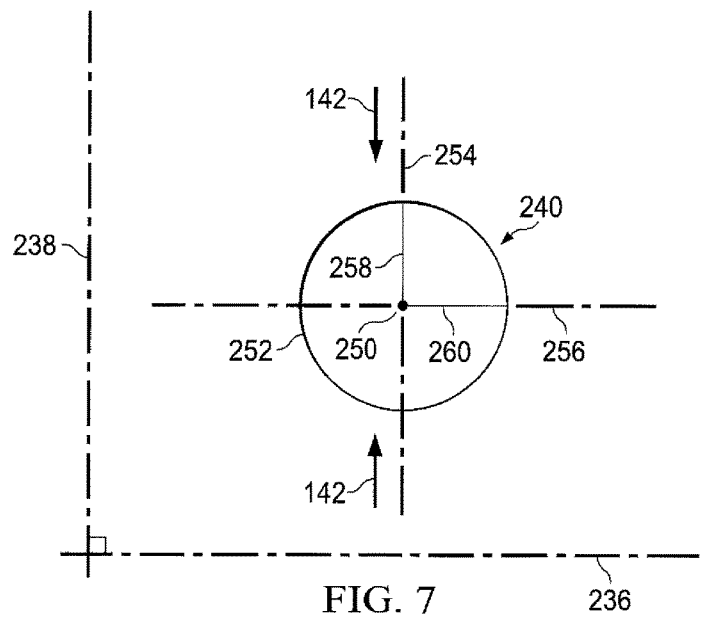
FIG. 7 is a schematic view, illustrating details that may be associated with some embodiments of a hole of the debridement tool of FIG. 6.

Referring more specifically to FIG. 7, a single hole 240 having a circular shape is shown. The hole 240 may include a center 250, a perimeter 252, and a perforation shape factor (PSF). For reference, the hole 240 may have an X-axis 256 extending through the center 250 parallel to the first orientation line 236, and a Y-axis 254 extending through the center 250 parallel to the second orientation line 238. In some embodiments, the perforation shape factor (PSF) of the hole 240 may be defined as a ratio of a line segment 258 on the Y-axis 254 extending from the center 250 to the perimeter 252 of the hole 240, to a line segment 260 on the X-axis 256 extending from the center 250 to the perimeter 252 of the hole 240. If a length of the line segment 258 is 2.5 mm and the length of the line segment 260 is 2.5 mm, the perforation shape factor (PSF) would be 2.5/2.5 or about 1.

Figure 8:
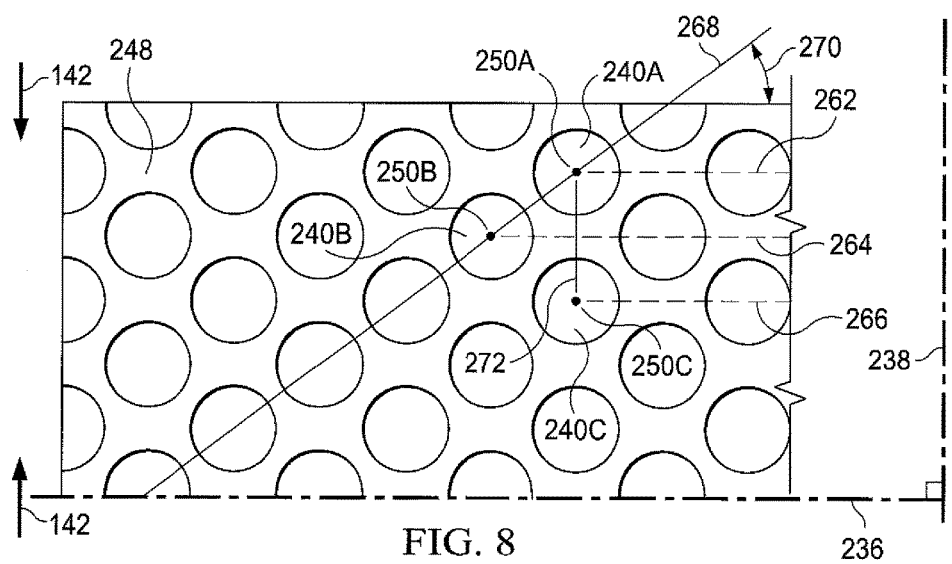
FIG. 8 is a plan view, illustrating details that may be associated with some embodiments of the holes of the debridement tool of FIG. 6.

Referring to FIG. 8, a portion of the debridement tool 210 of FIG. 6 is shown. The debridement tool 210 may include the plurality of holes 240 aligned in a pattern of parallel rows. The pattern of parallel rows may include a first row 262 of the holes 240, a second row 264 of the holes 240, and a third row 266 of the holes 240. The X-axis 256 of FIG. 7 of each hole 240 may be parallel to the first orientation line 236 of FIG. 8. The centers 250 of the holes 240 in adjacent rows, for example, the first row 262 and the second row 264, may be characterized by being offset from the second orientation line 238 along the first orientation line 236. In some embodiments, a line connecting the centers of adjacent rows may form the strut angle (SA) with the first orientation line 236. For example, a first hole 240A in the first row 262 may have a center 250A, and a second hole 240B in the second row 264 may have a center 250B. A strut line 268 may connect the center 250A with the center 250B. The strut line 268 may form an angle 270 with the first orientation line 236. The angle 270 may be the strut angle (SA) of the debridement tool 210. In some embodiments, the strut angle (SA) may be less than about 90°. In other embodiments, the strut angle (SA) may be between about 30° and about 70° relative to the first orientation line 236. As described above, if negative pressure is applied to the debridement tool 210, the debridement tool 210 may be more compliant or compressible in a direction perpendicular to the first orientation line 236. By increasing the compressibility of the debridement tool 210 in a direction perpendicular to the first orientation line 236, the debridement tool 210 may collapse to apply a debriding force to the tissue site 103 as described in more detail below.

In some embodiments, the centers 250 of the holes 240 in alternating rows, for example, the center 250A of the first hole 240A in the first row 262 and a center 250C of a hole 240C in the third row 266, may be spaced from each other parallel to the second orientation line 238 by a length 272. In some embodiments, the length 272 may be greater than an effective diameter of the hole 240. If the centers 250 of holes 240 in alternating rows are separated by the length 272, the walls 248 parallel to the first orientation line 236 may be considered continuous. Generally, the walls 248 may be continuous if the walls 248 do not have any discontinuities or breaks between holes 240.

Regardless of the shape of the holes 240, the holes 240 in the debridement tool 210 may leave void spaces in the debridement tool 210 and on the tissue-facing surface 211 of the debridement tool 210 so that only walls 248 of the debridement tool 210 remain with a surface available to contact the tissue site 103. It may be desirable to minimize the walls 248 so that the holes 240 collapse, causing the debridement tool 210 to collapse to generate the debriding force 142 in a direction perpendicular to the first orientation line 236. However, it may also be desirable not to minimize the walls 248 so much that the debridement tool 210 becomes too fragile for sustaining the application of a negative pressure. The void space percentage (VS) of the holes 240 may be equal to the percentage of the volume or surface area of the void spaces of the tissue-facing surface 211 created by the holes 240 to the total volume or surface area of the tissue-facing surface 211 of the debridement tool 210. In some embodiments, the void space percentage (VS) may be between about 40% and about 60%, In other embodiments, the void space percentage (VS) may be about 54%.

In some embodiments, a diameter of the holes 240 may be selected to permit flow of particulates through the holes 240. In some embodiments, each hole 240 may have a diameter of about 5 mm. In other embodiments, each hole 240 may have an effective diameter between about 3.5 mm and about 20 mm.

Referring now to both FIGS. 7 and 8, the holes 240 may form in a pattern depending on the geometry of the holes 240 and the alignment of the holes 240 between adjacent and alternating rows in the debridement tool 210 with respect to the first orientation line 236. If the debridement tool 210 is subjected to negative pressure, the holes 240 of the debridement tool 210 may collapse. In some embodiments, the void space percentage (VS), the perforation shape factor (PSF), and the strut angle (SA) may cause the debridement tool 210 to collapse along the second orientation line 238 perpendicular to the first orientation line 236. The debriding force 142 may be optimized by adjusting the factors described above as set forth in Table 1 below. In some embodiments, the holes 240 may be circular, have a strut angle (SA) of approximately 37°, a void space percentage (VS) of about 54%, a firmness factor (FF) of about 5, a perforation shape factor (PSF) of about 1, and a diameter of about 5 mm. If the debridement tool 210 is subjected to a negative pressure of about −125 mmHg, the debridement tool 210 asserts the debriding force 142 of approximately 11.9 N. If the diameter of the holes 240 of the debridement tool 210 is increased to about 20 mm, the void space percentage (VS) changed to about 52%, the strut angle (SA) changed to about 52°, and the perforation shape factor (PSF) and the firmness factor (FF) remain the same, the debriding force 142 is decreased to about 6.5 N.

Figure 9A:
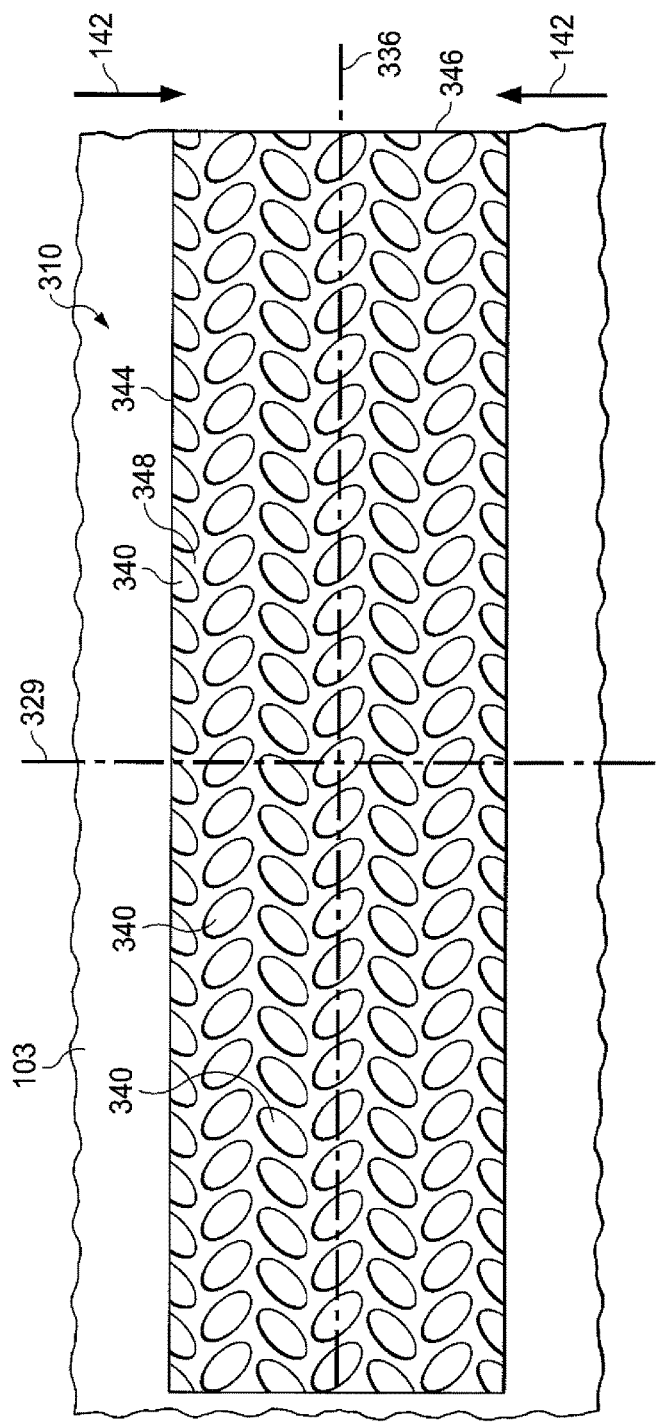
FIG. 9A is a plan view, illustrating details that may be associated with some embodiments of another debridement tool of the negative-pressure therapy system of FIG. 1.

FIG. 9A is a plan view, illustrating additional details that may be associated with some embodiments of a debridement tool 310. The debridement tool 310 may be similar to the debridement tool 110 and operate as described above with respect to FIGS. 1-5, Similar elements may have similar reference numbers indexed to 300. The debridement tool 310 may cover the tissue site 103. In some embodiments, the debridement tool 310 may have a first orientation line 336 and a second orientation line 338 that is perpendicular to the first orientation line 336. In some embodiments, the first orientation line 336 and the second orientation line 338 may be used to refer to the desired directions of contraction for the debridement tool 310. For example, the desired direction of contraction may be parallel to the second orientation line 338 and perpendicular to the first orientation line 336. In other embodiments, the desired direction of contraction may be perpendicular to the second orientation line 338 and parallel to the first orientation line 336. In still other embodiments, the desired direction of contraction may be at a non-perpendicular angle to both the second orientation line 338 and the first orientation line 336. Generally, the debridement tool 310 may be placed at the tissue site 103 so that a tissue-facing surface 311 of the debridement tool 310 may cover portions of the tissue site 103 having slough 130 and eschar 132. The debridement tool 310 may include a plurality of holes 340 or perforations extending through the debridement tool 310 to form walls 348 that extend through the debridement tool 310. In some embodiments, the walls 348 are parallel to the thickness 334 of the debridement tool 310. The walls 348 may have transverse surfaces that intersect with the tissue-facing surface 311 to form cutting edges. In some embodiments, the holes 340 may have an ovoid shape as shown.

Figure 10:
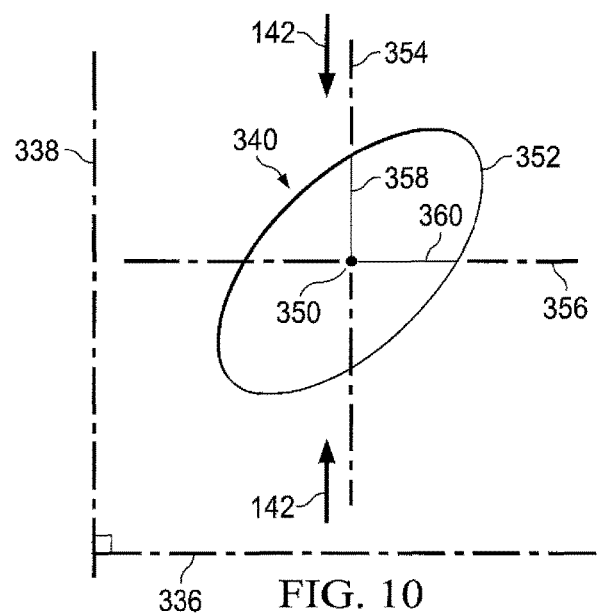
FIG. 10 is a schematic view, illustrating details that may be associated with some embodiments of a hole of the debridement tool of FIG. 9A having a perforation shape factor.

Referring more specifically to FIG. 10, a single hole 340 having an ovoid shape is shown. The hole 340 may include a center 350, a perimeter 352, and a perforation shape factor (PSF). For reference, the hole 340 may have an X-axis 356 extending through the center 350 parallel to the first orientation line 336, and a Y-axis 354 extending through the center 350 parallel to the second orientation line 338. In some embodiments, the perforation shape factor (PSF) of the hole 340 may be defined as a ratio of a line segment 358 on the Y-axis 354 extending from the center 350 to the perimeter 352 of the hole 340, to a line segment 360 on the X-axis 356 extending from the center 350 to the perimeter 352 of the hole 340. If a length of the line segment 358 is 2.5 mm and the length of the line segment 360 is 2.5 mm, the perforation shape factor (PSF) would be 2.5/2.5 or about 1.

Figure 11:
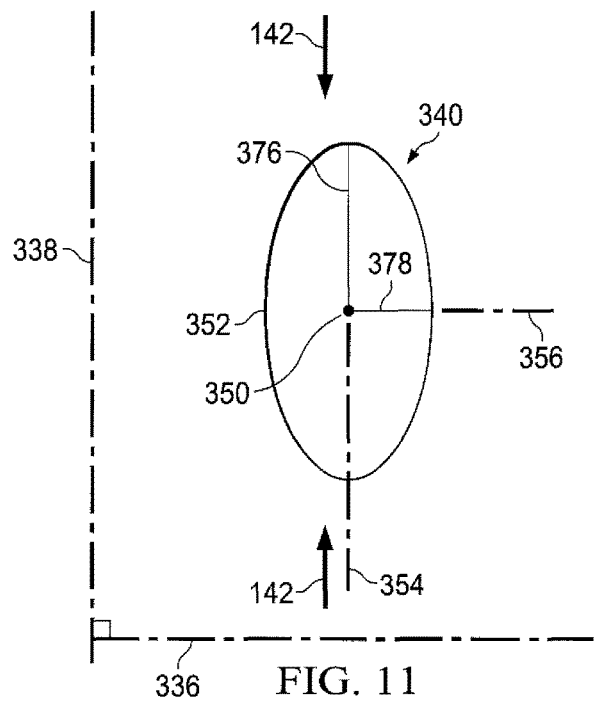
FIG. 11 is a schematic view, illustrating details that may be associated with some embodiments of a hole of the debridement tool of FIG. 9A having another perforation shape factor.

Referring to FIG. 11, if the hole 340 is rotated relative to the first orientation line 336 and the second orientation line 338 so that a major axis of the hole 340 is parallel to the second orientation line 338 and a minor axis of the hole 340 is parallel to the first orientation line 336, the perforation shape factor (PSF) may change. For example, the perforation shape factor (PSF) is now the ratio of a line segment 376 on the Y-axis 354 extending from the center 350 to the perimeter 352 of the hole 340, to a line segment 378 on the X-axis 356 extending from the center 350 to the perimeter 352 of the hole 340. If a length of the line segment 376 is 5 mm and the length of the line segment 378 is 2.5 mm, the perforation shape factor (PSF) would be 5/2.5 or about 2.

Figure 12:
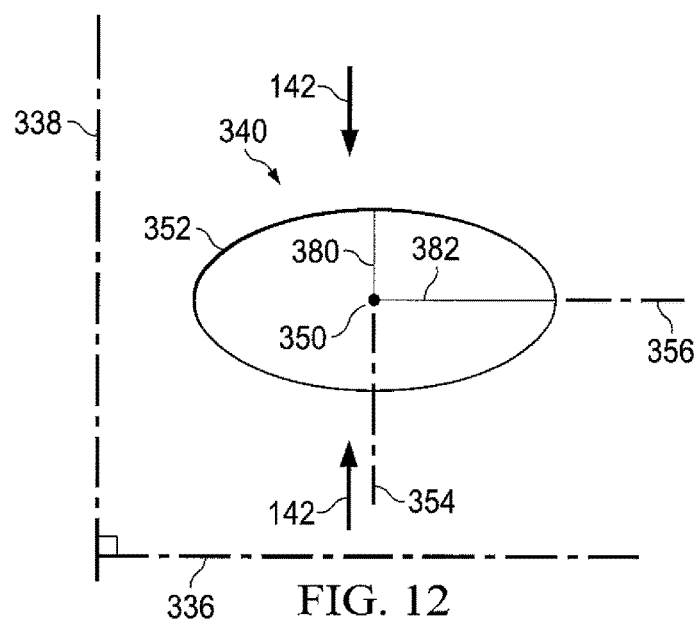
FIG. 12 is a schematic view, illustrating details that may be associated with some embodiments of a hole of the debridement tool of FIG. 9A having another perforation shape factor.

Referring to FIG. 12, if the hole 340 is rotated relative to the first orientation line 336 and the second orientation line 338 so that a major axis of the hole 340 is parallel to the first orientation line 336 and a minor axis of the hole 340 is parallel to the second orientation line 338, the perforation shape factor (PSF) may change. For example, the perforation shape factor (PSF) is now the ratio of a line segment 380 on the Y-axis 354 extending from the center 350 to the perimeter 352 of the hole 340, to a line segment 382 on the X-axis 356 extending from the center 350 to the perimeter 352 of the hole 340. If a length of the line segment 380 is 2.5 nun and the length of the line segment 382 is 5 mm, the perforation shape factor (PSF) would be 2.5/5 or about ½.

Figure 9B:
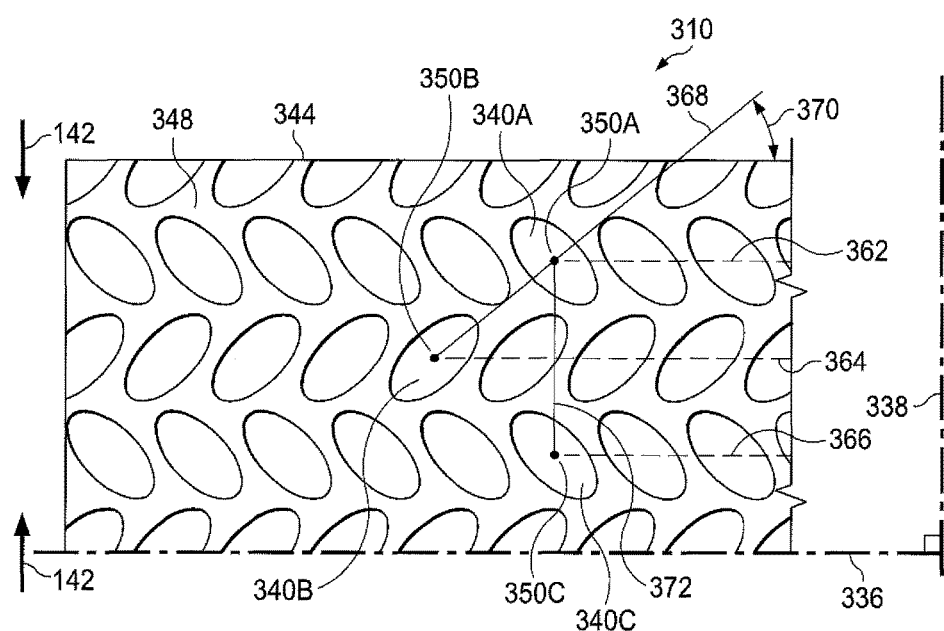
FIG. 9B is a plan view, illustrating details that may be associated with some embodiments of the holes of the debridement tool of FIG. 9A.

Referring to FIG. 9B, a portion of the debridement tool 310 of FIG. 9A is shown. The debridement tool 310 may include the plurality of holes 340 aligned in a pattern of parallel rows. The pattern of parallel rows may include a first row 262 of the holes 340, a second row 364 of the holes 340, and a third row 366 of the holes 340. The X-axis 356 of each hole 340 of FIGS. 10, 11, and 12 may be parallel to the first orientation line 336 of FIG. 9B. The centers 350 of the holes 340 in adjacent rows, for example, the first row 262 and the second row 364, may be characterized by being offset from the second orientation line 338 along the first orientation line 336. In some embodiments, a line connecting the centers of adjacent rows may form a strut angle (SA) with the first orientation line 336. For example, a first hole 340A in the first row 262 may have a center 350A, and a second hole 340B in the second row 364 may have a center 350B. A strut line 368 may connect the center 350A with the center 350B.

The strut line 368 may form an angle 370 with the first orientation line 336. The angle 370 may be the strut angle (SA) of the debridement tool 310. In some embodiments, the strut angle (SA) may be less than about 90°. In other embodiments, the strut angle (SA) may be between about 30° and about 70° relative to the first orientation line 336. As described above, if negative pressure is applied to the debridement tool 310, the debridement tool 310 may be more compliant or compressible in a direction perpendicular to the first orientation line 336. By increasing the compressibility of the debridement tool 310 in a direction perpendicular to the first orientation line 336, the debridement tool 310 may collapse to apply the debriding force 142 to the tissue site 103 as described in more detail below.

In some embodiments, the centers 350 of the holes 340 in alternating rows, for example, the center 350A of the first hole 340A in the first row 262 and a center 350C of a hole 340C in the third row 366, may be spaced from each other parallel to the second orientation line 338 by a length 372. In some embodiments, the length 372 may be greater than an effective diameter of the hole 340. If the centers 350 of holes 340 in alternating rows are separated by the length 372, the walls 348 parallel to the first orientation line 336 may be considered continuous. Generally, the walls 348 may be continuous if the walls 348 do not have any discontinuities or breaks between holes 340.

Regardless of the shape of the holes 340, the holes 340 in the debridement tool 310 may leave void spaces in the debridement tool 310 and on the tissue-facing surface 311 of the debridement tool 310 so that only walls 348 of the debridement tool 310 remain with a surface available to contact the tissue site 103. It may be desirable to minimize the walls 348 so that the holes 340 may collapse, causing the debridement tool 310 to collapse the debriding force 142 in a direction perpendicular to the first orientation line 336. However, it may also be desirable not to minimize the walls 348 so much that the debridement tool 310 becomes too fragile for sustaining the application of a negative pressure. The void space percentage (VS) of the holes 340 may be equal to the percentage of the volume or surface area of the void spaces of the tissue-facing surface 311 created by the holes 340 to the total volume or surface area of the tissue-facing surface 311 of the debridement tool 310. In some embodiments, the void space percentage (VS) may be between about 40% and about 60%. In other embodiments, the void space percentage (VS) may be about 56%.

In some embodiments, an effective diameter of the holes 340 may be selected to permit flow of particulates through the holes 340. In some embodiments, each hole 340 may have an effective diameter of about 7 mm. In other embodiments, each hole 340 may have an effective diameter between about 2.5 mm and about 20 mm.

Referring now to both FIGS. 9A and 9B, the holes 340 may form a pattern depending on the geometry of the holes 340 and the alignment of the holes 340 between adjacent and alternating rows in the debridement tool 310 with respect to the first orientation line 336. If the debridement tool 310 is subjected to negative pressure, the holes 340 of the debridement tool 310 may collapse, causing the debridement tool 310 to collapse along the second orientation line 338 perpendicular to the first orientation line 336. If the debridement tool 310 is positioned on the tissue site 103, the debridement tool 310 may generate the debriding force 142 along the second orientation line 338 such that the debridement tool 310 is contracted in the same direction to debride the tissue site 103. The debriding force 142 may be optimized by adjusting the factors described above as set forth in Table 1 below. In some embodiments, the holes 340 may be ovular, have a strut angle (SA) of approximately 47°, a void space percentage (VS) of about 56%, a firmness factor (FF) of about 5, a perforation shape factor (PSF) of about 1, and an effective diameter of about 7 mm (where the major axis is about 10 mm and the minor axis is about 5 mm). If the debridement tool 310 is subjected to a negative pressure of about −125 mmHg, the debridement tool 310 asserts the debriding force 142 of approximately 13.5 N.

Figure 13A:
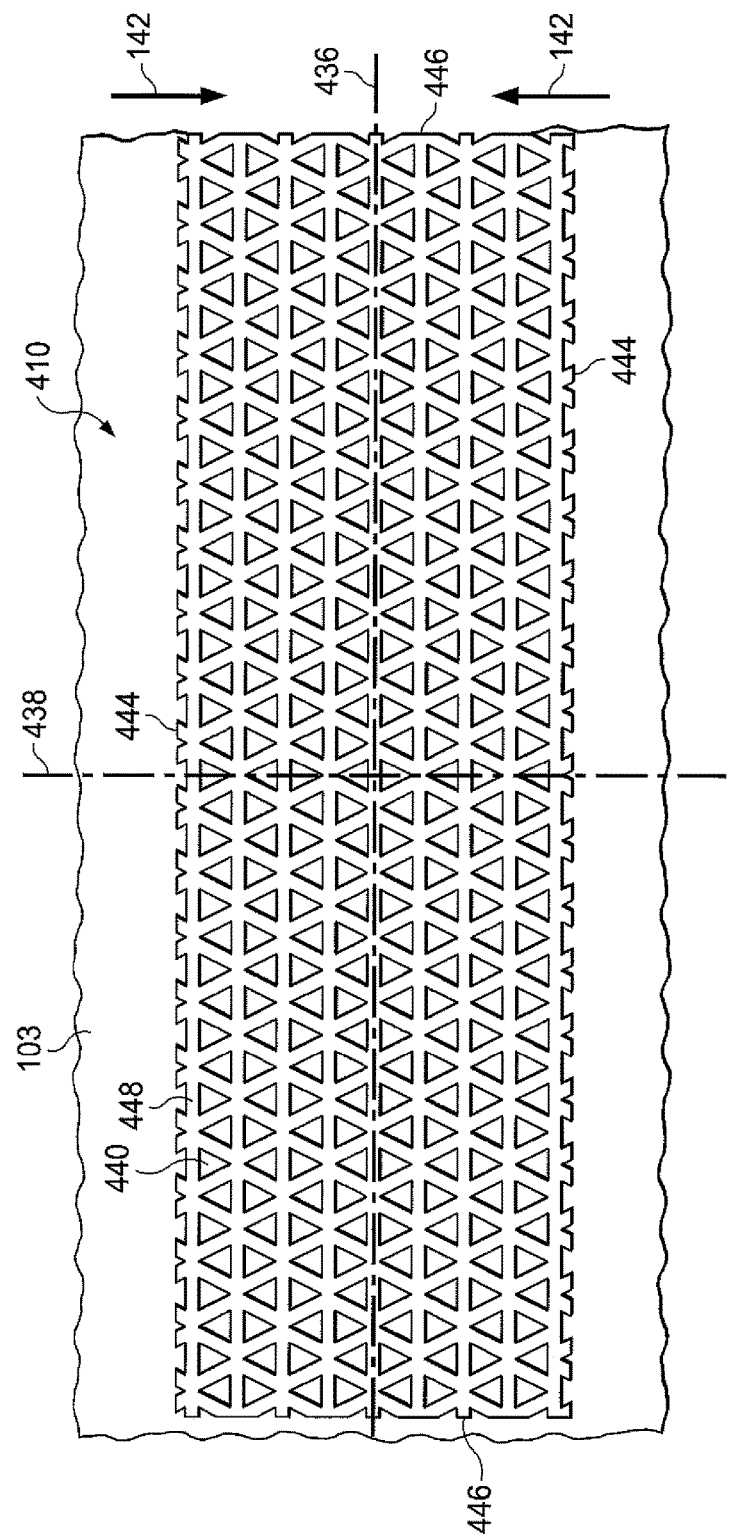
FIG. 13A is a plan view, illustrating details that may be associated with some embodiments of another debridement tool of the negative-pressure therapy system of FIG. 1.
Figure 14:
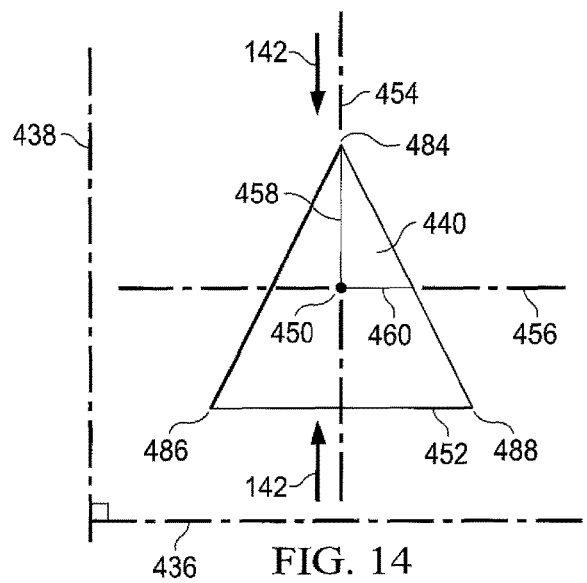
FIG. 14 is a schematic view, illustrating details that may be associated with some embodiments of a hole of the debridement tool of FIG. 13A.

FIG. 13A is a plan view, illustrating additional details that may be associated with some embodiments of a debridement tool 410. The debridement tool 410 may be similar to the debridement tool 110 and operate as described with respect to FIGS. 1-5. Similar elements may have similar reference numbers indexed to 400. For example, the debridement tool 410 is shown as having a generally rectangular shape including longitudinal edges 444 and latitudinal edges 446. The debridement tool 410 may cover the tissue site 103. In some embodiments, the debridement tool 410 may have a first orientation line 436 and a second orientation line 438 that is perpendicular to the first orientation line 436. In some embodiments, the first orientation line 436 and the second orientation line 438 may be used to refer to the desired directions of contraction for the debridement tool 410. For example, the desired direction of contraction may be parallel to the second orientation line 438 and perpendicular to the first orientation line 436. In other embodiments, the desired direction of contraction may be perpendicular to the second orientation line 438 and parallel to the first orientation line 436. In still other embodiments, the desired direction of contraction may be at a non-perpendicular angle to both the second orientation line 438 and the first orientation line 436. Generally, the debridement tool 410 may be placed at the tissue site 103 so that a tissue-facing surface 411 of the debridement tool 410 may cover portions of the tissue site 103 having slough 130 or eschar 132. The debridement tool 410 may include a plurality of holes 440 or perforations extending through the debridement tool 410 to form walls 448 that extend through the debridement tool 410. In some embodiments, the walls 448 are parallel to the thickness 434 of the debridement tool 410. The walls 448 may have transverse surfaces that intersect with the tissue-facing surface 411 to form cutting edges, In some embodiments, the holes 440 may have a triangular shape as shown, Referring more specifically to FIG. 14, a single hole 440 having a triangular shape is shown. The hole 440 may include a center 450, a perimeter 452, and a perforation shape factor (PSF). In some embodiments, the hole 440 may include a first vertex 484, a second vertex 486, and a third vertex 488. For reference, the hole 440 may have an X-axis 456 extending through the center 450 parallel to the first orientation line 436, and a Y-axis 454 extending through the center 450 parallel to the second orientation line 438. In some embodiments, the perforation shape factor (PSF) of the hole 440 may be defined as a ratio of a line segment 458 on the Y-axis 454 extending from the center 450 to the perimeter 452 of the hole 440, to a line segment 460 on the X-axis 456 extending from the center 450 to the perimeter 452 of the hole 440. If a length of the line segment 458 is 1.1 mm and the length of the line segment 460 is 1 mm, the perforation shape factor (PSF) would be 1.1/1 or about 1.1.

Figure 13B:
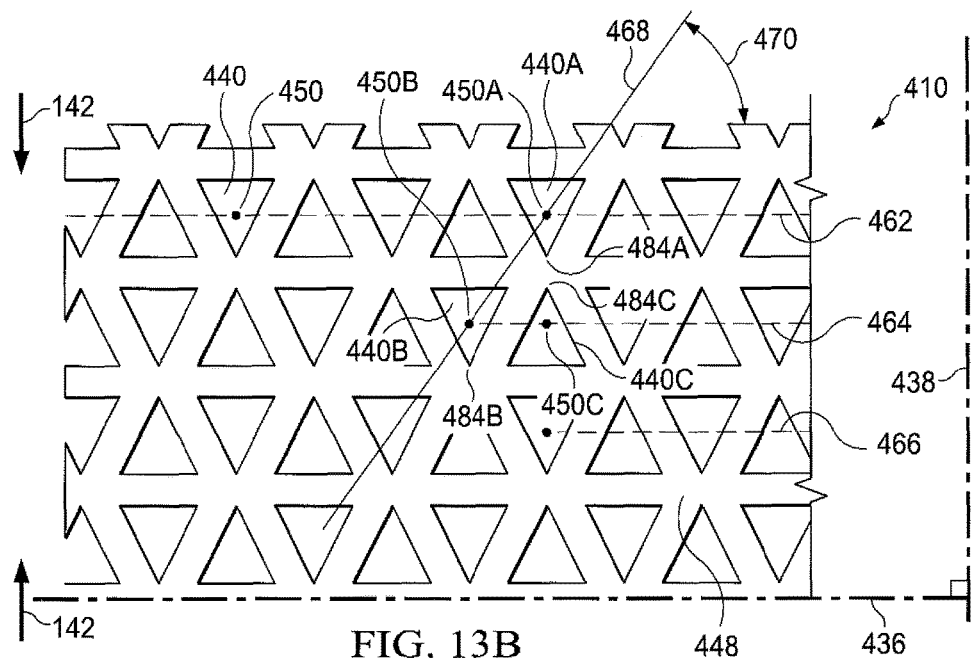
FIG. 13B is a plan view, illustrating details that may be associated with some embodiments of the holes of the debridement tool of FIG. 13A.

Referring to FIG. 13B, a portion of the debridement tool 410 of FIG. 13A is shown. The debridement tool 410 may include the plurality of holes 440 aligned in a pattern of parallel rows. The pattern of parallel rows may include a first row 462 of the holes 440, a second row 464 of the holes 440, and a third row 466 of the holes 440. The X-axis 456 of FIG. 14 of each hole 440 may be parallel to the first orientation line 436 of FIG. 13B. In some embodiments, a first hole 440A in the first row 462 may be oriented so that the first vertex 484A may be between the first orientation line 436 and a leg of the first hole 440A opposite the first vertex 484A. A hole 440C that is adjacent the first hole 440A in the first row 462 may be oriented so that the first vertex 484C may be oriented opposite the first hole 440A.

The centers 450 of the holes 440 in adjacent rows having the first vertex 484 oriented in a same direction, for example, the first row 462 and the second row 464, may be characterized by being offset from the second orientation line 438 along the first orientation line 436. In some embodiments, a line connecting the centers 450 of adjacent rows may form a strut angle (SA) with the first orientation line 436. For example, a first hole 440A in the first row 462 may have a center 450A, and a second hole 440B in the second row 464 may have a center 450B and a first vertex 484B. A strut line 468 may connect the center 450A with the center 450B. The strut line 468 may form an angle 470 with the first orientation line 436. The angle 470 may be the strut angle (SA) of the debridement tool 410. In some embodiments, the strut angle (SA) may be less than about 90°. In other embodiments, the strut angle (SA) may be between about 40° and about 70° relative to the first orientation line 436. As described above, if negative pressure is applied to the debridement tool 410, the debridement tool 410 may be more compliant or compressible in a direction perpendicular to the first orientation line 436. By increasing the compressibility of the debridement tool 410 in a direction perpendicular to the first orientation line 436, the debridement tool 410 may collapse to apply the debriding force 142 to the tissue site 103 as described in more detail below.

Regardless of the shape of the holes 440, the holes 440 in the debridement tool 410 may leave void spaces in the debridement tool 410 and on the tissue-facing surface 411 of the debridement tool 410 so that only the walls 448 of the debridement tool 410 remain with a surface available to contact the tissue site 103. It may be desirable to minimize the walls 448 so that the holes 440 may collapse, causing the debridement tool 410 to generate the debriding force 142 in a direction perpendicular to the first orientation line 436. However, it may also be desirable not to minimize the walls 448 so much that the debridement tool 410 becomes too fragile for sustaining the application of a negative pressure. The void space percentage (VS) of the holes 440 may be equal to the percentage of the volume or surface area of the void spaces of the tissue-facing surface 411 created by the holes 440 to the total volume or surface area of the tissue-facing surface 411 of the debridement tool 410. In some embodiments, the void space percentage (VS) may be between about 40% and about 60%. In other embodiments, the void space percentage (VS) may be about 56%.

In some embodiments, an effective diameter of the holes 440 may be selected to permit flow of particulates through the holes 440. In some embodiments, each hole 440 may have an effective diameter of about 7 mm. In other embodiments, each hole 440 may have an effective diameter between about 2.5 mm and about 20 mm.

Referring now to both FIGS. 13A and 13B, the holes 440 may form a pattern depending on the geometry of the holes 440 and the alignment of the holes 440 between adjacent and alternating rows in the debridement tool 410 with respect to the first orientation line 436. If the debridement tool 410 is subjected to negative pressure, the holes 440 of the debridement tool 410 may collapse. In some embodiments, the void space percentage (VS), the perforation shape factor (PSF), and the strut angle (SA) may cause the debridement tool 410 to collapse along the second orientation line 438 perpendicular to the first orientation line 436. If the debridement tool 410 is positioned on the tissue site 103, the debridement tool 410 may generate the debriding force 142 along the second orientation line 438 such that the debridement tool 410 is contracted in the same direction. The debriding force 142 may be optimized by adjusting the factors described above as set forth in Table 1 below. In some embodiments, the holes 440 may be triangular, have a strut angle (SA) of approximately 63°, a void space percentage (VS) of about 40%, a firmness factor (FF) of 5, a perforation shape factor (PSF) of 1.1, and an effective diameter of about 10 mm. If the debridement tool 410 is subjected to a negative pressure of about −125 mmHg, the debridement tool 410 may assert the debriding force 142 of approximately 13.5 N.

Figure 15:
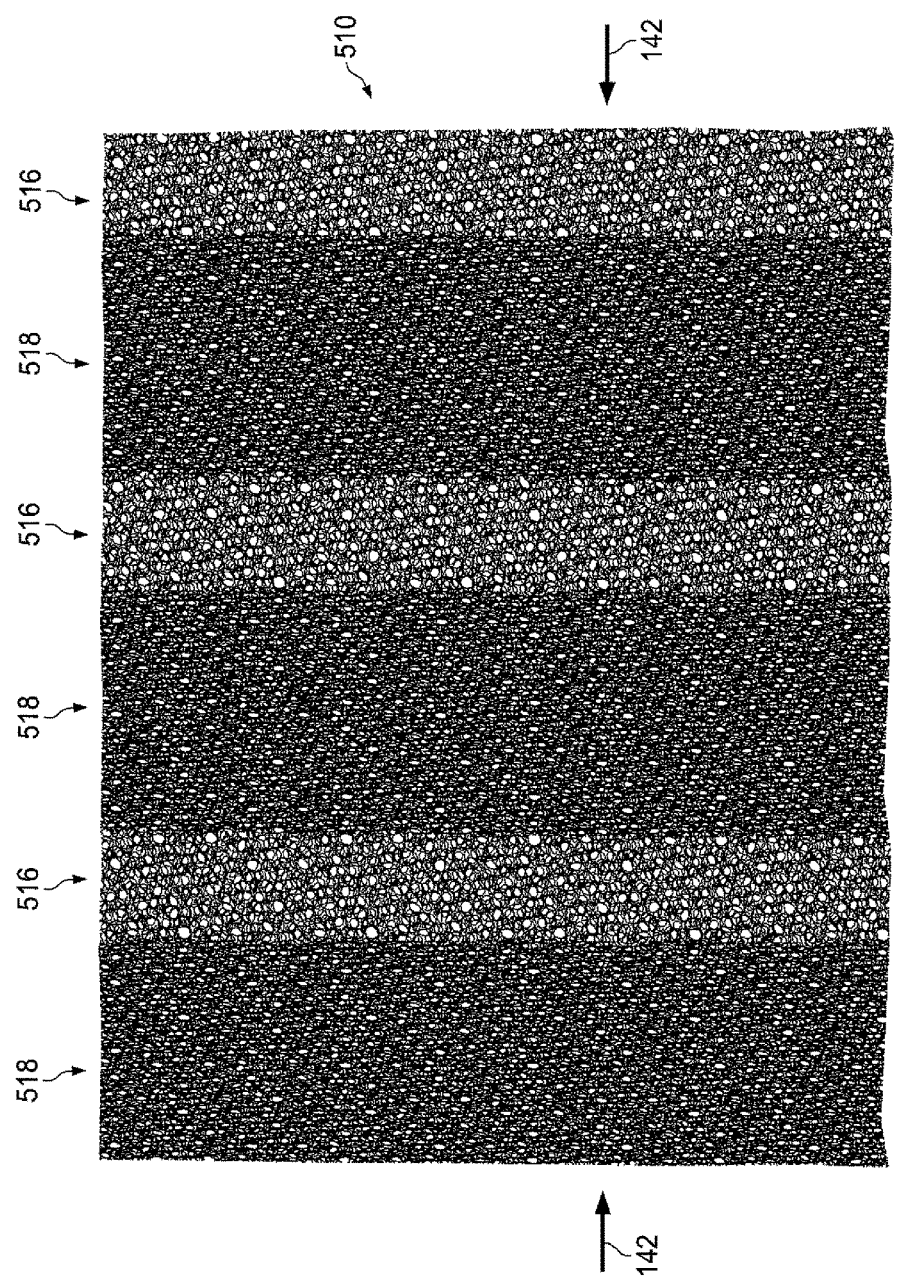
FIG. 15 is a plan view, illustrating details that may be associated with some embodiments of another debridement tool of the negative-pressure therapy system of FIG. 1.

FIG. 15 is a plan view, illustrating additional details that may be associated with some embodiments of a debridement tool 510. The debridement tool 510 may be similar to the debridement tool 110 described above with respect to FIGS. 1-5. The debridement tool 510 may include stripes 516 and stripes 518. In some embodiments, the debridement tool 510 may be formed from a foam, similar to GranuFoam®. In some embodiments, the stripes 518 may be formed by compressing portions of the foam so that the stripes 516 have a first density and the stripes 518 have a second density. In some embodiments, the second density is greater than the first density, for example. In some embodiments, the second density may be between about 3 times and about 5 times greater than the first density. For example, the stripes 516 may be an uncompressed foam, and the stripes 518 may be a compressed foam having a firmness factor of about 5. Generally, the stripes 516 may be more compressible than the stripes 518. In some embodiments, the stripes 516 and the stripes 518 may be vertically oriented relative to a tissue site, and in other embodiments, the stripes 516 and the stripes 518 may be horizontally oriented relative to a tissue site. In still other embodiments, the stripes 516 and the stripes 518 may be oriented at an angle relative to a tissue site. The foam material of the debridement tool 510 may have cutting edges formed by pores in the foam material that are positioned on a tissue-facing surface 511 of the debridement tool 510. If the debridement tool 510 is placed under a negative-pressure, the stripes 516 may collapse before the stripes 518. In some embodiments, if the stripes 516 collapse, the debridement tool 510 contracts perpendicular to the stripes 516. If the debridement tool 510 is cycled between contracted and relaxed states, as described above, the cutting edges of the pores may debride tissue similar to the cutting edges of the debridement tool 110, described above.

A debriding force, such as the debriding force 142, generated by a debridement tool, such as the debridement tool 110, may be related to a compressive force generated by applying negative pressure at a therapy pressure to a sealed therapeutic environment. For example, the debriding force 142 may be proportional to a product of a therapy pressure (TP) in the sealed therapeutic environment 128, the compressibility factor (CF) of the debridement tool 110, and a surface area (A) the tissue-facing surface 111 of the debridement tool 110. The relationship is expressed as follows:

$$\text{Debriding force } \alpha(TP*CF*A)$$

In some embodiments, the therapy pressure TP is measured in $N/m^2$, the compressibility factor (CF) is dimensionless, the area (A) is measured in $m^2$, and the debriding force is measured in Newtons (N). The compressibility factor (CF) resulting from the application of negative pressure to a debridement tool may be, for example, a dimensionless number that is proportional to the product of the void space percentage (VS) of a debridement tool, the firmness factor (FF) of the debridement tool, the strut angle (SA) of the holes in the debridement tool, and the perforation shape factor (PSF) of the holes in the debridement tool. The relationship is expressed as follows:

$$\text{Compressibility Factor (CF) } \alpha(VS*FF*\sin(SA)*PSF)$$

Based on the above formulas, debridement tools formed from different materials with holes of different shapes were manufactured and tested to determine the debriding force of the debridement tools. For each debridement tool, the therapy pressure TP was about −125 mmHg and the dimensions of the debridement tool were about 200 mm by about 53 mm so that the surface area (A) of the tissue-facing surface of the debridement tool was about 106 $cm^2$ or 0.0106 $m^2$. Based on the two equations described above, the debriding force for a Supracor® debridement tool 110 having a firmness factor (FF) of 3 was about 13.3 where the Supracor® debridement tool 110 had hexagonal holes 140 with a distance between opposite vertices of 5 mm, a perforation shape factor (PSF) of 1.07, a strut angle (SA) of approximately 66°, and a void space percentage (VS) of about 55%. A similarly dimensioned GranuFoam® debridement tool 110 generated the debriding force 142 of about 9.1 Newtons (N).

TABLE 1

| Material | VS | FF | SA | Hole Shape | PSF | Major diam. (mm) | Debriding force |
|---|---|---|---|---|---|---|---|
| GranuFoam ® | 56 | 5 | 47 | Ovular | 1 | 10 | 13.5 |
| Supracor ® | 55 | 3 | 66 | Hexagon | 1.1 | 5 | 13.3 |
| GranuFoam ® | 40 | 5 | 63 | Triangle | 1.1 | 10 | 12.2 |
| GranuFoam ® | 54 | 5 | 37 | Circular | 1 | 5 | 11.9 |
| GranuFoam ® | 52 | 5 | 37 | Circular | 1 | 20 | 10.3 |
| Grey Foam | N/A | 5 | N/A | Horizontal stripes | N/A | N/A | 9.2 |
| GranuFoam ® | 55 | 5 | 66 | Hexagon | 1.1 | 5 | 9.1 |
| GranuFoam ® | N/A | 5 | N/A | Horizontal stripes | N/A | N/A | 8.8 |
| Zotefoam | 52 | 3 | 37 | Circular | 1 | 10 | 8.4 |
| GranuFoam ® | 52 | 5 | 37 | Circular | 1 | 10 | 8.0 |
| GranuFoam ® | 52 | 5 | 64 | Circular | 1 | 10 | 7.7 |
| GranuFoam ® | 56 | 5 | 66 | Hexagon | 1.1 | 10 | 7.5 |
| Grey Foam | N/A | 3 | N/A | Horizontal stripes | N/A | N/A | 7.2 |
| Zotefoam | 52 | 3 | 52 | Circular | 1 | 20 | 6.8 |
| GranuFoam ® | N/A | 3 | N/A | Horizontal Striping | N/A | N/A | 6.6 |
| GranuFoam ® | 52 | 5 | 52 | Circular | 1 | 20 | 6.5 |
| GranuFoam ® | N/A | 5 | N/A | Vertical Stripes | N/A | N/A | 6.1 |

TABLE 1-continued

| Material | VS | FF | SA | Hole Shape | PSF | Major diam. (mm) | Debriding force |
|---|---|---|---|---|---|---|---|
| GranuFoam ® | N/A | 1 | N/A | None | N/A | N/A | 5.9 |
| GranuFoam ® | N/A | 3 | N/A | Vertical stripes | N/A | N/A | 5.6 |
| GranuFoam ® | 52 | 1 | 37 | None | 1 | 10 | 5.5 |

In some embodiments, the formulas described above may not precisely describe the debriding forces due to losses in force due to the transfer of the force from the debridement tool to the wound. For example, the modulus and stretching of the cover 106, the modulus of the tissue site 103, slippage of the cover 106 over the tissue site 103, and friction between the debridement tool 110 and the tissue site 103 may cause the actual value of the debriding force 142 to be less than the calculated value of the debriding force 142.

The systems, apparatuses, and methods described herein may provide significant advantages. For example, Combining the mechanical rubbing action of a debridement tool with the hydrating and flushing action of instillation and negative-pressure therapy may enable low or no pain debridement of a tissue site. A debridement tool as described herein may also require less monitoring from a clinician or other attendant as compared to other mechanical debridement processes and enzymatic debridement processes. In addition, debridement tools as described herein may not become blocked by removed necrotic tissue as may occur during autolytic debridement of a tissue site.

While shown in a few illustrative embodiments, a person having ordinary skill in the art will recognized that the systems, apparatuses, and methods described herein are susceptible to various changes and modifications. Moreover, descriptions of various alternatives using teems such as "or" do not require mutual exclusivity unless clearly required by the context, and the indefinite articles "a" or "an" do not limit the subject to a single instance unless clearly required by the context.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A system for debriding a tissue site, comprising:
a manifold adapted to deliver negative pressure to the tissue site;
a cover adapted to form a sealed space over the manifold and the tissue site for receiving a negative pressure from a negative-pressure source;
a debridement tool adapted to be positioned between the manifold and the tissue site and having a tissue-facing surface and an opposite surface including a plurality of holes extending through the debridement tool from the tissue-facing surface to the opposite surface, wherein each of the plurality of holes is separated from each other by walls, the walls having transverse surfaces extending between the tissue-facing surface and the opposite surface that form cutting edges with the tissue-facing surface, and wherein each of the plurality of holes has a perforation shape factor that allows each of the plurality of holes to collapse from a relaxed position to a contracted position in response to an application and removal of negative pressure from the sealed space; and
wherein the cutting edges are adapted to debride the tissue site in response to movement of the debridement tool between the relaxed position and the contracted position.

2. The system of claim 1, wherein each of the plurality of holes is adapted to collapse from the relaxed position to the contracted position generally perpendicular to a line of symmetry of the debridement tool.

3. The system of claim 1, wherein the plurality of holes have the perforation shape factor and a strut angle that are adapted to collapse each of the plurality of holes from the relaxed position to the contracted position.

4. The system of claim 1, wherein:
the plurality of holes are adapted to have the perforation shape factor and a strut angle configured to allow each of the plurality of holes to collapse from the relaxed position to the contracted position; and
each of the plurality of holes is adapted to collapse from the relaxed position to the contracted position generally perpendicular to a line of symmetry of the debridement tool.

5. The system of claim 3, wherein the strut angle is about 90 degrees.

6. The system of claim 3, wherein the strut angle is less than about 90 degrees.

7. The system of claim 1, further comprising a fluid source adapted to be fluidly coupled to the sealed space to provide fluid to the sealed space.

8. The system of claim 1, wherein each of the plurality of holes has an average effective diameter of about 5 mm.

9. The system of claim 1, wherein holes of the plurality of holes are formed in two or more parallel rows.

10. The system of claim 1, wherein the perforation shape factor of each of the plurality of holes is less than about 1.

11. The system of claim 1, wherein a thickness of the debridement tool is about 15 mm.

12. The system of claim 1, wherein a firmness factor of the debridement tool is about 5.

13. The system of claim 1, wherein a firmness factor of the debridement tool is about 3.

14. The system of claim 1, wherein a shape of each of the plurality of holes is hexagonal.

15. The system of claim 1, wherein a shape of each of the plurality of holes is elliptical.

16. The system of claim 1, wherein a shape of each of the plurality of holes is circular.

17. The system of claim 1, wherein a shape of each of the plurality of holes is triangular.

18. The system of claim 1, wherein the debridement tool comprises a compressed foam.

19. The system of claim 1, wherein the debridement tool comprises a felted foam.

20. The system of claim 1, wherein the debridement tool comprises a 3D spacer fabric.

21. The system of claim 1, wherein the debridement tool comprises a thermoplastic elastomer.

22. The system of claim 1, wherein the debridement tool comprises a thermoplastic polyurethane.

* * * * *